(12) United States Patent
Vestgaarden

(10) Patent No.: US 10,555,821 B2
(45) Date of Patent: Feb. 11, 2020

(54) METHOD AND APPARATUS FOR SPINAL INTERBODY FUSION INCLUDING FIXATION OR LOCKING PLATE

(76) Inventor: Tov Inge Vestgaarden, Madeira Beach, FL (US)

(*) Notice: Subject to any disclaimer, the term of this patent is extended or adjusted under 35 U.S.C. 154(b) by 0 days.

(21) Appl. No.: 13/238,524

(22) Filed: Sep. 21, 2011

(65) Prior Publication Data
US 2013/0073045 A1    Mar. 21, 2013

(51) Int. Cl.
*A61F 2/44*    (2006.01)

(52) U.S. Cl.
CPC .................................... *A61F 2/447* (2013.01)

(58) Field of Classification Search
CPC .......... A61F 2/44; A61F 2/442; A61F 2/4425; A61F 2/4455; A61F 2/446; A61F 2/447; A61F 2/4611; A61F 2002/443; A61F 2002/4475; A61F 2002/448; A61F 2220/0025
USPC ............................................ 623/17.11–17.16
See application file for complete search history.

(56) References Cited

U.S. PATENT DOCUMENTS

| | | | | |
|---|---|---|---|---|
| 5,683,394 | A * | 11/1997 | Rinner | 606/86 R |
| 7,621,938 | B2 * | 11/2009 | Molz, IV | 606/246 |
| 7,918,891 | B1 | 4/2011 | Curran et al. | |
| 2002/0161441 | A1 | 10/2002 | Lang et al. | |
| 2003/0195632 | A1 | 10/2003 | Foley et al. | |
| 2005/0159813 | A1 | 7/2005 | Molz, IV | |
| 2007/0010889 | A1 * | 1/2007 | Francis | 623/17.16 |
| 2008/0114456 | A1 * | 5/2008 | Dewey | A61B 17/7065 623/17.16 |
| 2008/0132949 | A1 | 6/2008 | Aferzon et al. | |
| 2008/0161926 | A1 | 7/2008 | Melkent et al. | |
| 2008/0183211 | A1 | 7/2008 | Lamborne et al. | |
| 2008/0269898 | A1 | 10/2008 | Carls et al. | |
| 2009/0187247 | A1 | 7/2009 | Metcalf, Jr. et al. | |

(Continued)

FOREIGN PATENT DOCUMENTS

| | | |
|---|---|---|
| EP | 2 758 006 | 8/2018 |
| WO | WO 2011/028306 | 3/2011 |

OTHER PUBLICATIONS

International Search Report and Written Opinion dated Feb. 26, 2013 for corresponding PCT International Patent Application No. PCT/US2012/056304 with an international filing date of Sep. 20, 2012.

(Continued)

*Primary Examiner* — Kevin T Truong
*Assistant Examiner* — Tracy L Kamikawa
(74) *Attorney, Agent, or Firm* — Pandiscio & Pandiscio

(57) ABSTRACT

A spinal fusion implant has a parallelepiped main body with a rotatably mounted retention plate secured to its distal end. The distal retention plate has a first position co-planar with the main body and a second, deployed position normal to the plane of the main body. The distal retention plate is in the first position when the main body is inserted between adjacent vertebral bodies and is in the second position after the main body is inserted between adjacent vertebral bodies. In further embodiments, a proximal retention plate is permanently deployed in normal relation to the main body or both the distal and proximal retention plates are rotatably mounted and both are deployed co-planar to the main body before insertion and normal to the main body after insertion.

5 Claims, 35 Drawing Sheets

(56) References Cited

U.S. PATENT DOCUMENTS

| | | | |
|---|---|---|---|
| 2009/0234389 A1* | 9/2009 | Chuang | A61B 17/7065 606/249 |
| 2010/0241166 A1 | 9/2010 | Dwyer et al. | |
| 2010/0318127 A1* | 12/2010 | Phan | A61B 17/7065 606/249 |
| 2011/0166600 A1 | 7/2011 | Lamborne et al. | |
| 2012/0004729 A1 | 1/2012 | Zipnick | |
| 2012/0221051 A1 | 8/2012 | Robinson | |
| 2012/0239089 A1 | 9/2012 | Druman et al. | |
| 2014/0324103 A1 | 10/2014 | Levieux et al. | |
| 2016/0367379 A1 | 12/2016 | Refai | |

OTHER PUBLICATIONS

Extended European Search Report for European Application No. 12833016 dated May 28, 2015; Applicant: Vestgaarden, Tov Inge.
Bolgova, M. V. et al., Age-Related Changes of Lumbar Vertebral Body Morphometry, Austin Journal of Anatomy, vol. 1, Iss. 3, 2014, pp. 1-7.

\* cited by examiner

METHOD AND APPARATUS FOR SPINAL INTERBODY FUSION INCLUDING FIXATION OR LOCKING PLATE

BACKGROUND OF THE INVENTION

1. Field of the Invention

This invention relates to surgical methods and apparatus in general, and more particularly to surgical methods and apparatus for fusing spinal vertebral bodies.

2. Brief Description of the Related Art

Disc herniation is a condition in which a spinal disc bulges from between two vertebral bodies and impinges on adjacent nerves, thereby causing pain. In some cases, non-operative procedures such as bed rest, medication, lifestyle modifications, exercise, physical therapy, chiropractic care and steroid injections may suffice. However, in other cases, surgical intervention may be necessary. In cases where surgical intervention is prescribed, spinal vertebral body fusion may be desirable, i.e., the spine may have deteriorated so much that adjacent vertebral bodies must be fused together.

Spinal fixation is the current standard of care for surgically treating disc herniation in patients who have chronic pain and who have, or are likely to develop, associated spinal instability. Spinal fixation procedures are intended to relieve impingement on nerves by removing the portion of the disc or bone, or both, responsible for compressing the neural structures and destabilizing the spine. The excised disc or bone is replaced with one or more intervertebral implants, or spacers, placed between adjacent vertebral bodies. These implants stabilize the adjacent vertebral bodies relative to one another so that the two vertebral bodies can fuse together.

One problem with spinal fixation is that the surgeon must make incisions on both sides of the spine. This lengthens the time required to perform an operation and it lengthens the patient's recovery time.

However, in view of the art considered as a whole at the time the present invention was made, it was not obvious to those of ordinary skill in the art how conventional surgical procedures could be improved.

SUMMARY OF THE INVENTION

The long-standing but heretofore unfulfilled need for an improved spinal fusion implant is now met by a new, useful, and non-obvious invention.

The novel spinal fusion implant preferably includes a substantially parallelepiped body, hereinafter referred to as the main body, having a predetermined length, width, and thickness. The main body may also have a cylindrical or oval shape. In some embodiments, the upper and lower surfaces may be oblique to one another so that a first side of the device may have more depth than a second side or a first end may have more depth than a second end.

In a first embodiment, a retention plate is rotatably secured to a distal end of the main body. The retention plate has a first, undeployed or unrotated position that is co-planar with the main body when the main body is being inserted into a gap between adjacent, spaced apart vertebral bodies and a second, deployed or rotated position that is misaligned from the main body, after the insertion has been completed, allowing the retention plate to engage adjacent, i.e., spaced apart vertebral bodies, thereby preventing retraction of the main body in a direction opposite to the direction of insertion.

The main body has an operative position between adjacent vertebral bodies when in use. The length of the main body is sufficient to span a distance between opposing cortical portions of a vertebral body without extending substantially beyond the vertebral body when the body is in the operative position. The thickness of the main body is substantially the same as a gap between opposing vertebral bodies in a spinal joint when the main body is in its operative position.

The retention plate is in its first, co-planar position when the main body is inserted between adjacent vertebral bodies and in its second, deployed position after the main body is inserted between adjacent vertebral bodies.

The spinal fusion implant is in the operative position after the insertion. The retention plate holds the spinal fusion implant and adjacent vertebral bodies in a stable relationship to one another when the retention plate is deployed in its second, misaligned position.

In further embodiments, a second retention plate located on the proximal end of the main body is employed. The distal retention plate is mounted in co-planar relation to the main body at the time of insertion but the proximal retention plate may be in its deployed position at the time of insertion.

In some embodiments, a rod ties the distal and proximal retention plates together so that after insertion, the proximal plate is deployed into its operative position and the distal retention plate is conjointly deployed therewith into its deployed position.

The novel spinal fusion implant is disposed between adjacent, i.e., opposing vertebral bodies to immobilize the affected segment and facilitate fusion between the opposing vertebral bodies when said novel spinal fusion implant is positioned in the gap between said adjacent vertebral bodies.

The spinal fusion implant can include gripping surfaces on the superior and inferior faces of the main body. The spinal fusion implant may also be provided with convex superior and inferior surfaces. It can also be tapered from the anterior to the posterior face. Moreover, the implant may also include an insertion tool guide.

An important object of the invention is to provide a spinal fusion implant that does not require incisions on both sides of a spine.

A more specific object is to provide a spinal fusion implant that is inserted from a proximal side of a spine and which has a retention plate mounted on the distal end that is retracted into co-planar relation with the implant main body when the implant is inserted and deployed into a misaligned relation to said implant main body after the insertion has been completed.

Another object is to provide an implant where retention plates are mounted to both the distal and proximal ends of the implant body and where said retention plates are in their respective retracted positions during insertion and in their respective deployed configurations after insertion.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the nature and objects of the invention, reference should be made to the following detailed disclosure, taken in connection with the accompanying drawings, in which.

DETAILED DESCRIPTION OF THE PREFERRED EMBODIMENT

Figure 1:
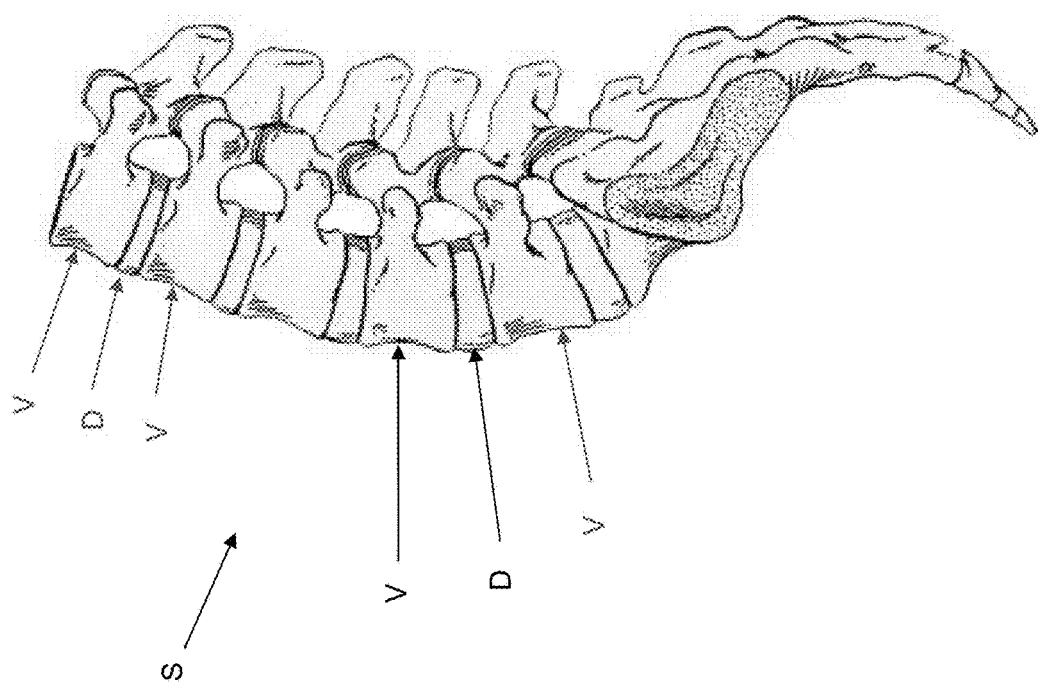
FIG. 1 a schematic view of a human spine.

FIG. 1 depicts a typical human spine S. Spine S includes a plurality of vertebral bodies V separated by discs D. A spine may deteriorate so much that adjacent vertebral bodies must be fused together. The novel spinal fusion implant is disposed between contiguous vertebral bodies to immobilize the affected segment of the spine and facilitate fusion between said contiguous vertebral bodies.

Figure 2:
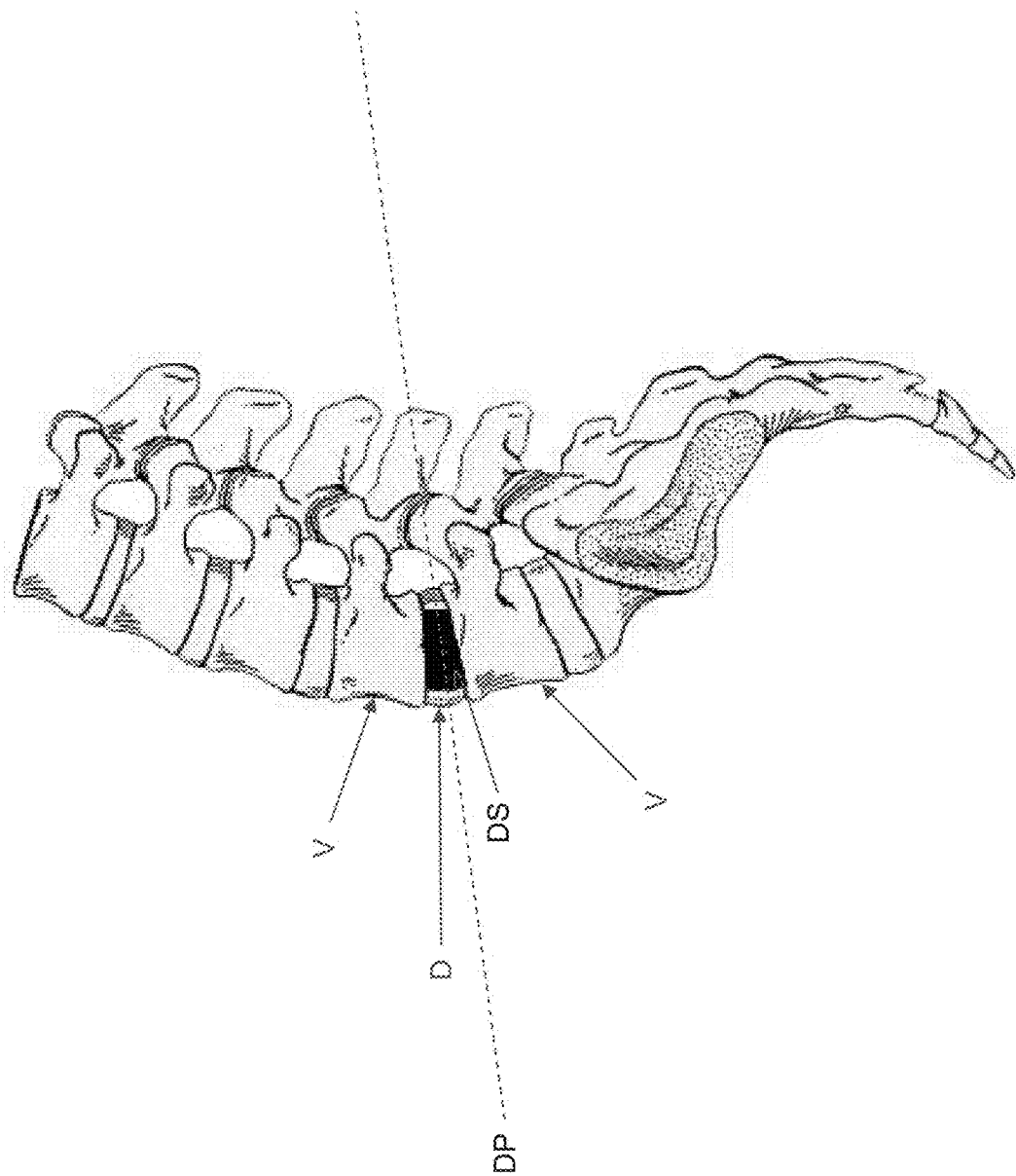
FIG. 2 is a schematic view illustrating the novel spinal fusion implant installed in a disc space.

FIG. 2 depicts the novel spinal fusion implant installed in a disc space. More particularly, spinal fusion implant 5 is disposed between two adjacent vertebral bodies V to stabilize those two vertebral bodies relative to one another and permit fusion of the same. The spine is prepared by removing some or all of the disc that resides in the space which is to be occupied by spinal fusion implant 5. The disc space DS is prepared with a rongeur or other surgical instrument.

The novel structure effectively stabilizes the joint but permits the occurrence of "micro-motion" between the opposing vertebral bodies, which is important for successful bone fusion.

Figure 3:
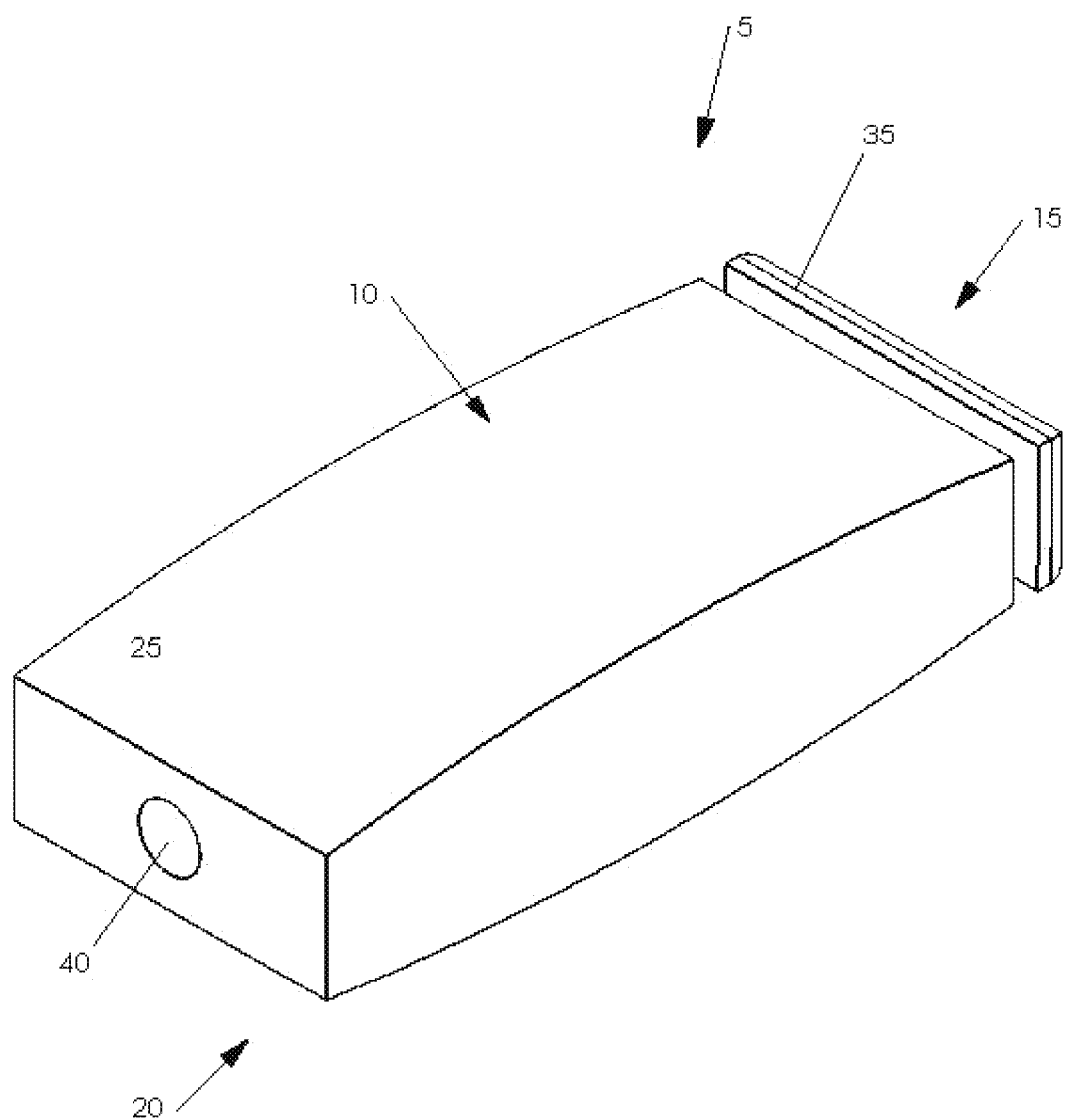
FIG. 3 is a perspective view of a first embodiment of the novel spinal fusion implant.
Figure 4:
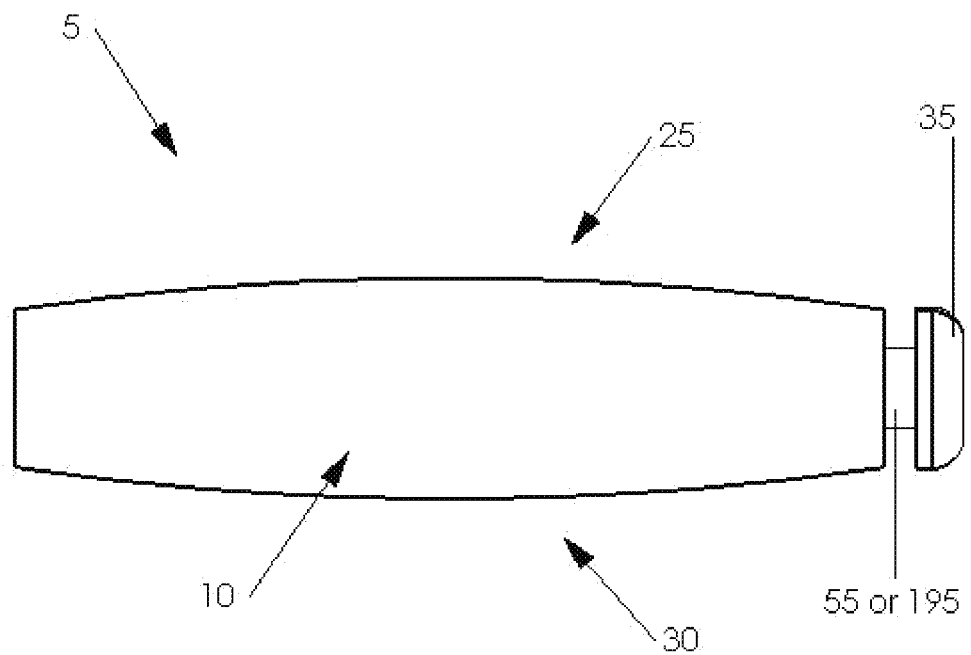
FIG. 4 is a side elevational view thereof.
Figure 5:
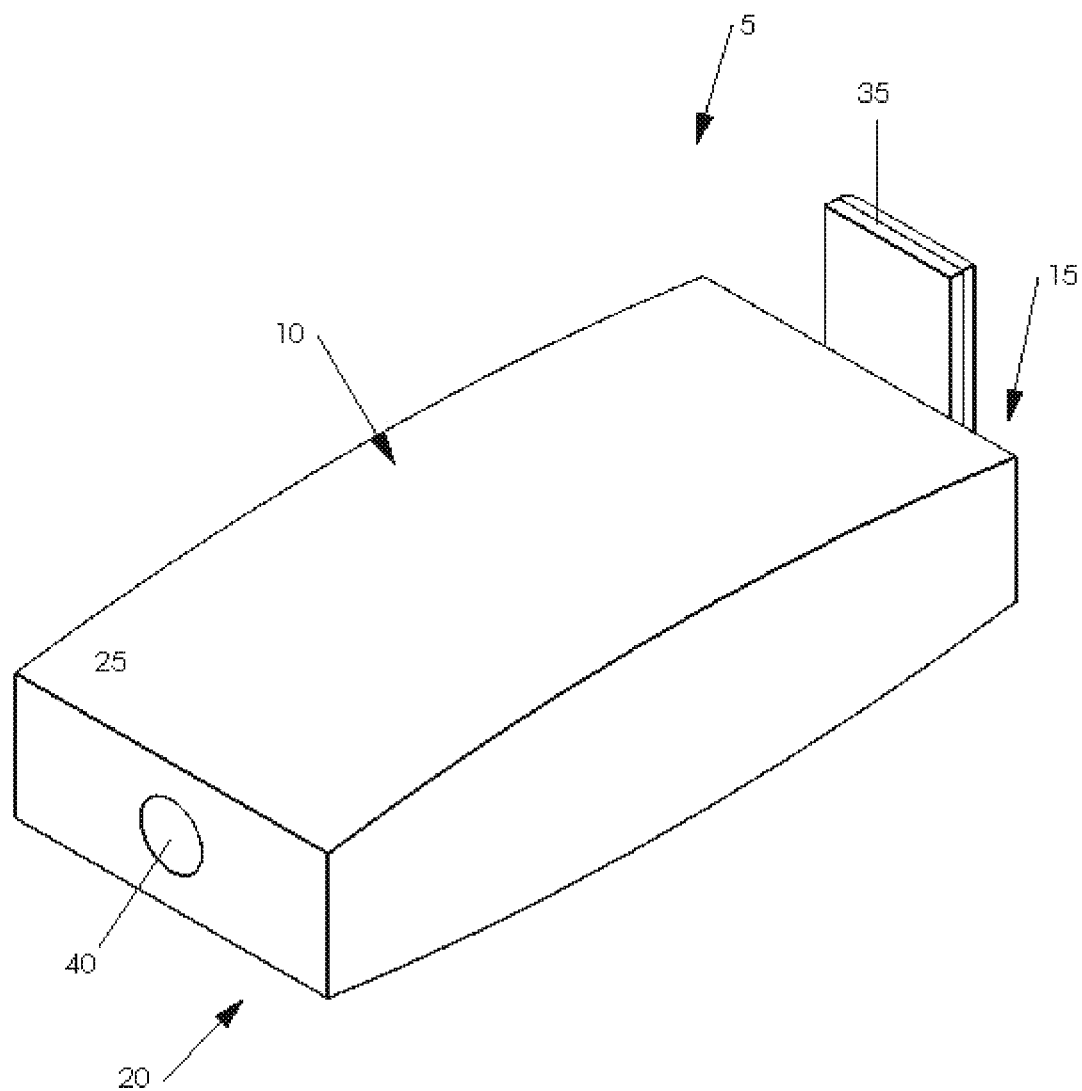
FIG. 5 is a perspective view similar to FIG. 3 but with the distal retention plate in its deployed configuration.
Figure 30:
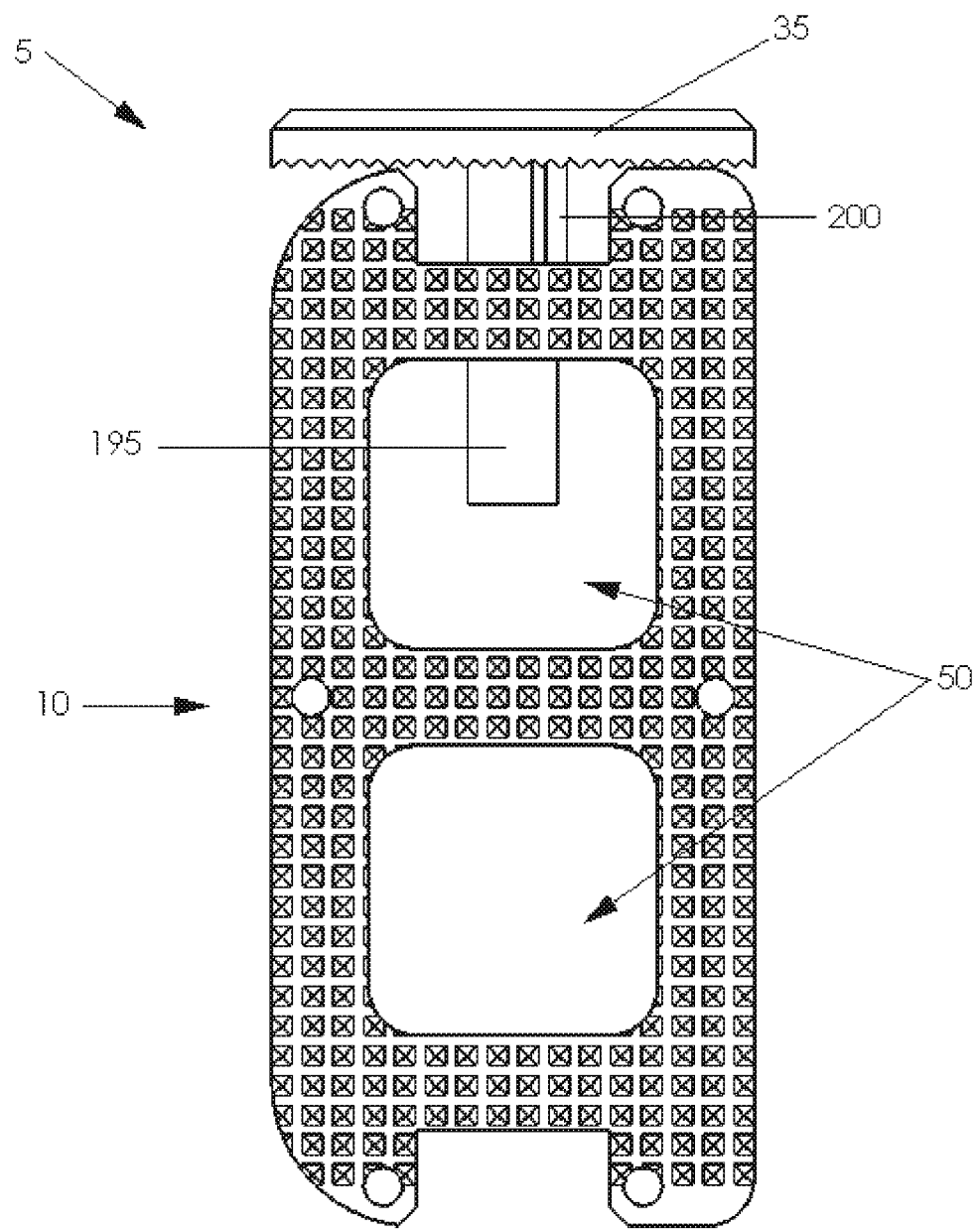
FIG. 30 is a top plan view of the fourteenth embodiment.

Referring now to FIGS. 3-5, which depict the most basic embodiment of spinal fusion implant 5, retention plate 35 is attached to main body 10 by either central rod 55 or short shaft 195 (see FIG. 30). An adjusting instrument may be inserted into instrument port 40 to slide retention plate 35 laterally and deploy said retention plate.

Implant 5 includes a generally parallelepiped main body 10 having a predetermined length, width and depth. Although not preferred, a circular or oval configuration is also within the scope of this invention and the top and bottom surfaces of main body 10 may also be oblique to one another. Main body 10 has distal end 15, proximal end 20, smooth upper surface 25, and smooth lower surface 30. Distal retention plate 35 is rotatably secured to main body 10 and main body 10 further includes instrument port 40 for deploying retention plate 35. Upper surface 25 and lower surface 30 are substantially parallel to one another but each surface is slightly convex as best understood in connection with FIGS. 3 and 4.

Retention plate 35 overlies and is mounted to distal end 15. Retention plate is in the non-rotated position depicted in FIGS. 3 and 4 when it is inserted between adjacent vertebrae. It is rotated into the FIG. 5 position after such insertion. However, the rotation of retention plate 35 need not be a full ninety degree (90°) rotation as depicted; any rotation that prevents retraction of said main body 10 is sufficient.

Misalignment (at least some rotation) of distal retention plate 35 from main body 10 limits motion in a multi-directional joint. More particularly, the shape of main body 10 limits motion in flexion/extension, while retention plate 35 limits lateral bending. This construction eliminates the possibility of eccentric forces inducing motion in the joint. Novel spinal fusion implant 5 may be manufactured in a wide range of sizes in order to accommodate any size of disc between the vertebral bodies.

The upper and lower surfaces 25, 35 of main body 10 may be formed with an inclined or non-parallel (oblique) configuration to provide the spinal fusion implant with an overall wedge shape in order to provide spinal curvature where desired.

Novel spinal fusion implant 5 may be constructed out of substantially any biocompatible material, including bone, which has properties consistent with the present invention including, but not limited to, ceramics, PEEK, stainless steel and titanium. Thus, the novel implant permits a surgeon to select a spinal fusion implant having the appropriate size and composition for a given intervertebral fusion. More particularly, the shape of main body 10 limits motion in flexion/extension, while retention plate 35 limits lateral bending. This construction eliminates the possibility of eccentric forces inducing motion in the joint.

The configuration of spinal fusion implant 5 may be varied without departing from the scope of the present invention.

Figure 7:
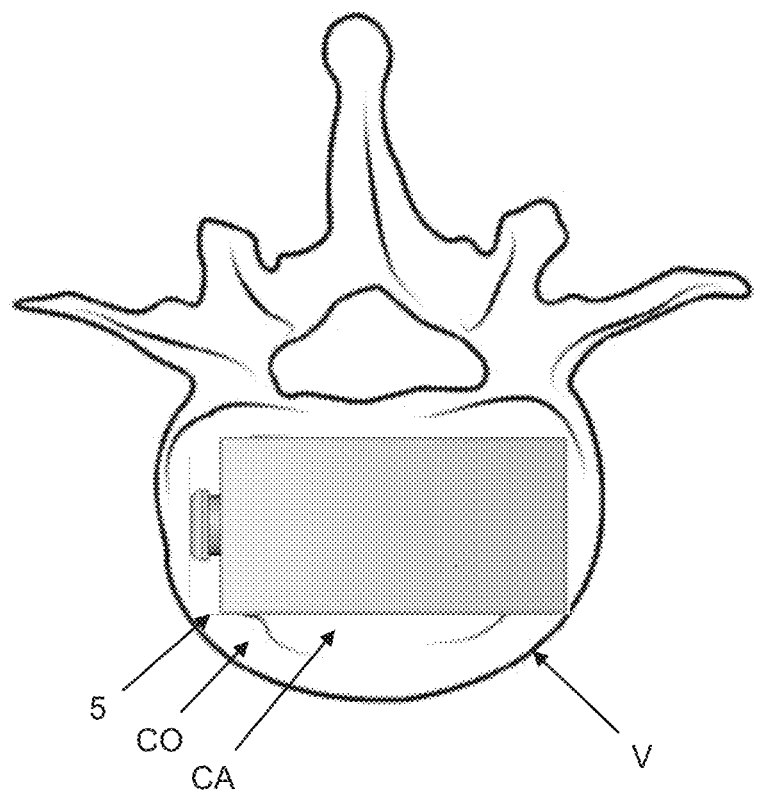
FIG. 7 is a schematic view illustrating the spinal fusion implant installed with the retention plate deployed inside of the vertebral body.

FIG. 7 is a schematic view depicting the spinal fusion implant installed with the retention plate deployed inside of the vertebral body.

Figure 8:
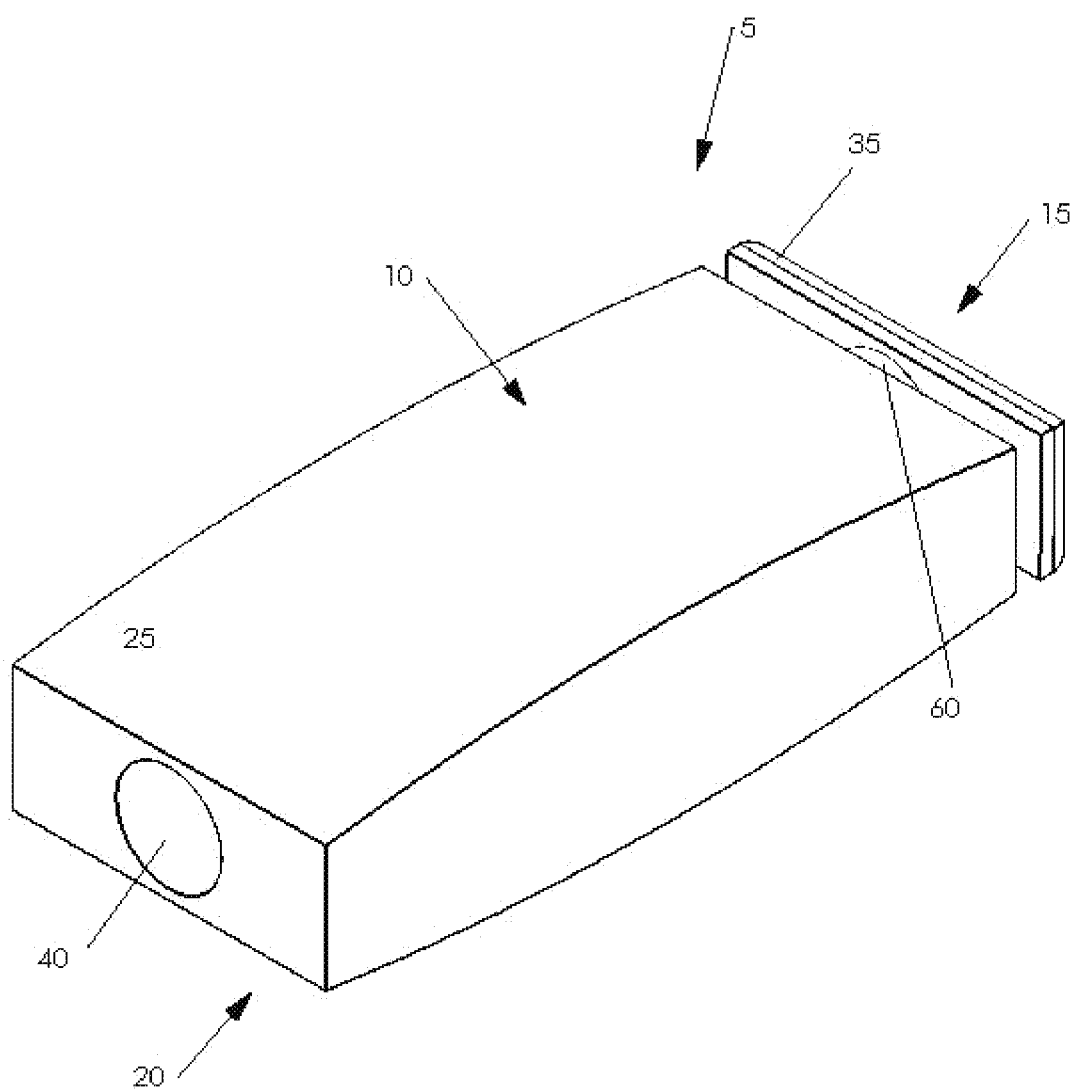
FIG. 8 is a perspective view of a second embodiment.
Figure 9:
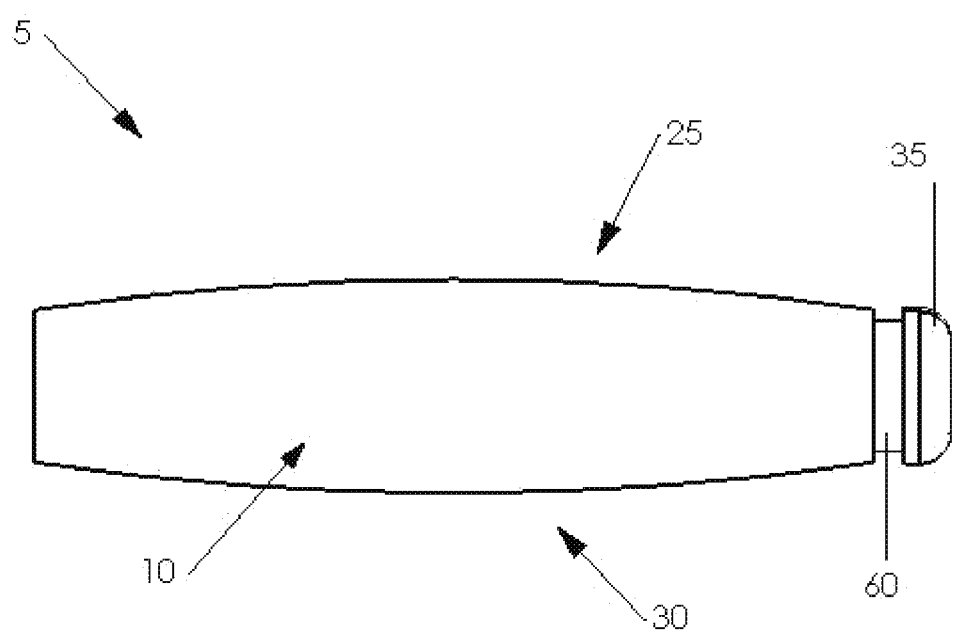
FIG. 9 is a side elevational view thereof.

The second embodiment is depicted in FIGS. 8 and 9. It differs from the first embodiment because it adds distal spacer 60.

Retention plate 35 is attached to adjustable width spacer 60 which slides laterally via an adjusting instrument inserted into instrument port 40. This configuration provides more effective vertebral resting due to the increased diameter of the adjustable width spacer 60.

Figure 10:
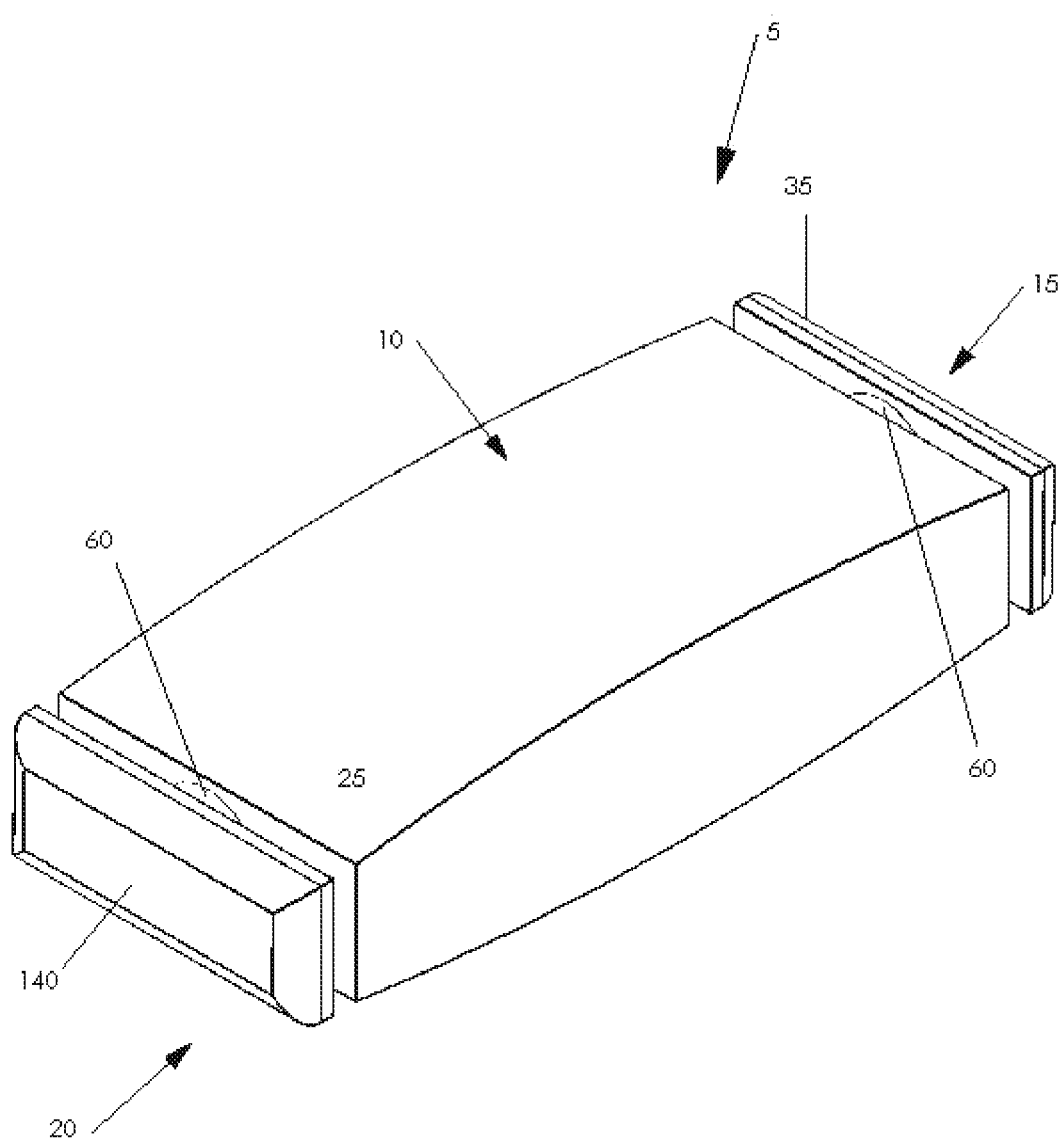
FIG. 10 is a perspective view of a third embodiment.

The third embodiment is depicted in FIG. 10. It differs from the second embodiment because it adds proximal retention plate 140 and a second proximal spacer 60.

Figure 11:
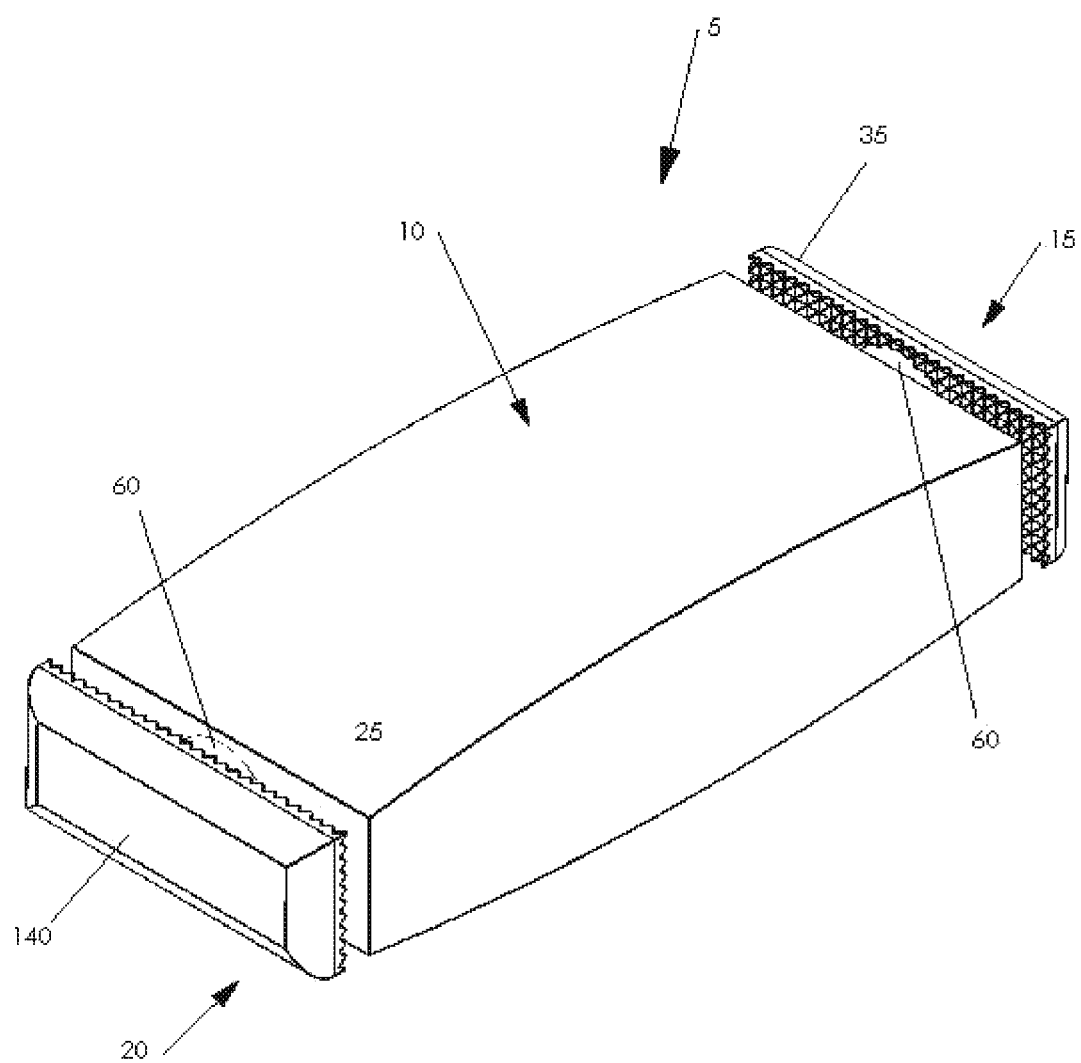
FIG. 11 is a perspective view of a fourth embodiment.

The fourth embodiment is depicted in FIG. 11. It adds a gripping surface to the respective inboard surfaces of distal retention plate 35 and proximal retention plate 140. No reference character is applied to said easily seen gripping surfaces to avoid clutter of the drawings.

Figure 12:
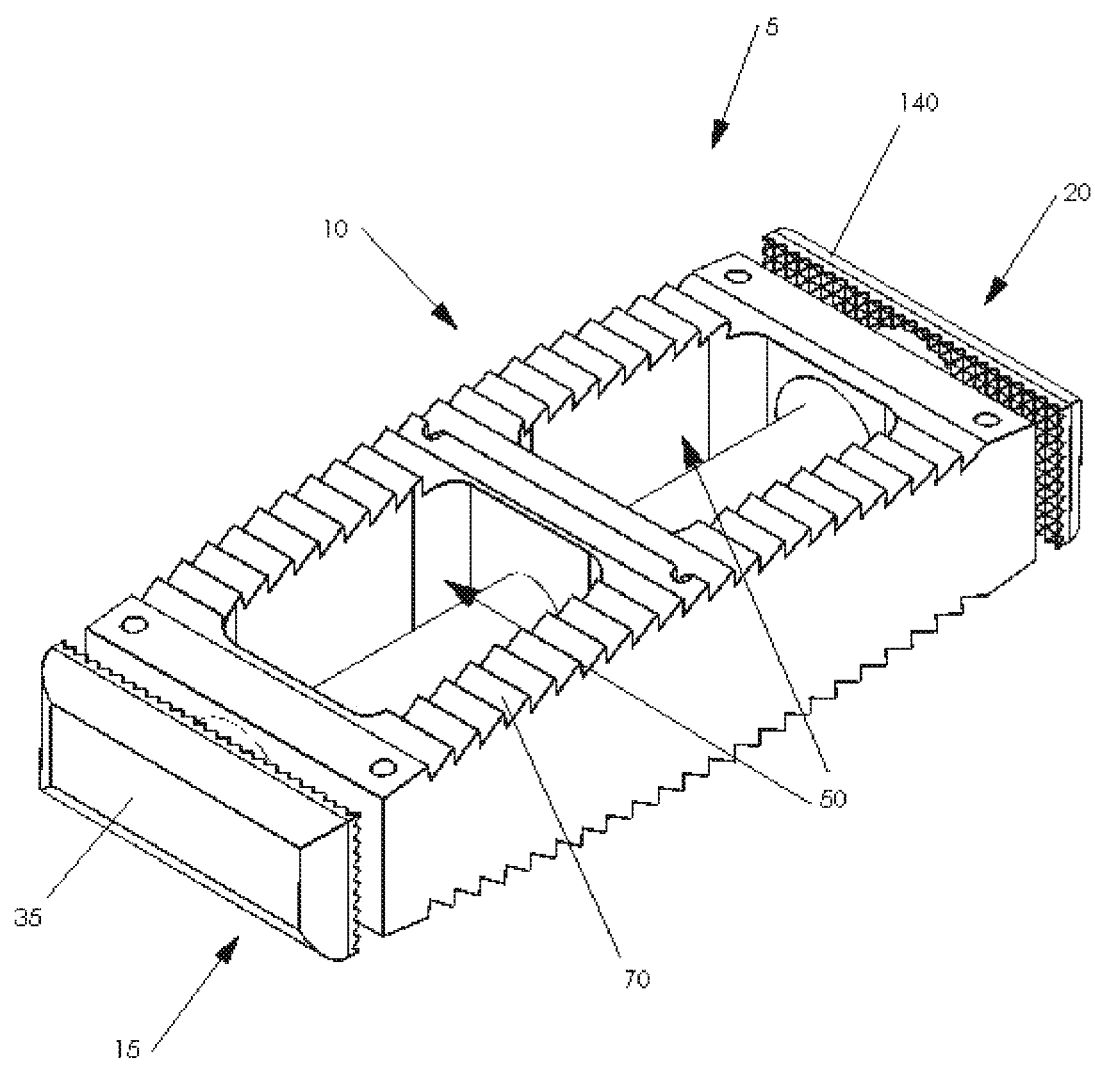
FIG. 12 is a perspective view of a fifth embodiment.
Figure 13:
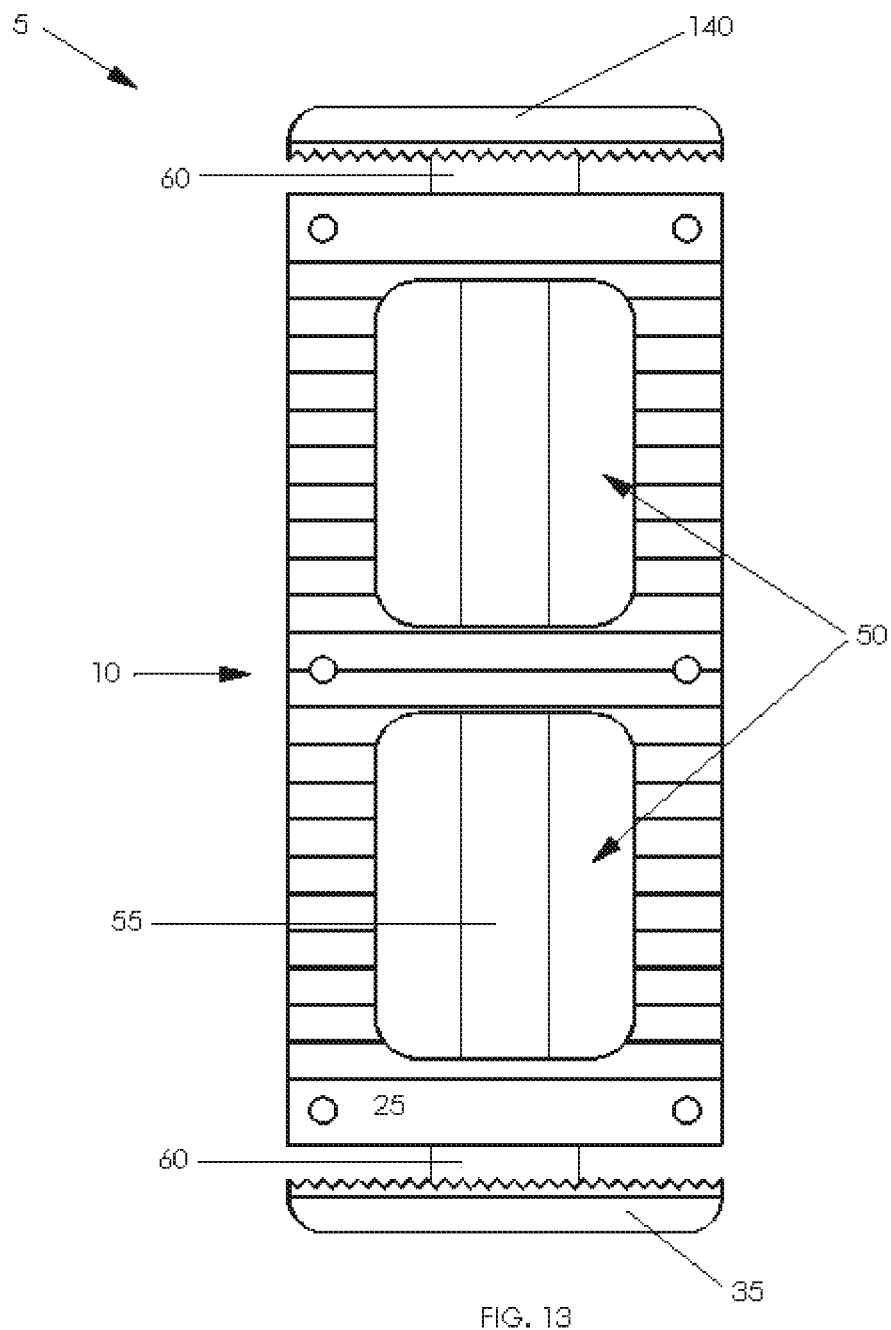
FIG. 13 is a top plan view of said fifth embodiment.

The fifth embodiment is depicted in FIGS. 12-13. This embodiment of spinal fusion implant 5 includes rod 55 mounted coincident with the longitudinal axis of symmetry of main body 10. Retention plate 35 is mounted at its center to the distal end of said rod but rod 55 does not protrude through plate 35. Rotation of said rod about its longitudinal axis of rotation is facilitated using proximal plate 140 and such rotation effects conjoint rotation of said retention plate 35. Rotation of rod 55 also advances or retracts said rod relative to said longitudinal axis.

This fifth embodiment further includes adjustable width spacers 60 at its distal end 15 and proximal end 20. Both retention plates 35 and 140 attach to rod 55 via said adjustable width spacer 60 as best depicted in FIGS. 12 and 13. Adjustable width spacer 60 has a larger diameter than rod 55, thereby providing a more effective vertebral resting surface.

Two apertures, collectively denoted 50, are formed in this fourth embodiment of spinal fusion implant 5 and extend completely therethrough. Apertures 50 preferably have a common shape and size and are disposed on opposite sides of and in equidistantly spaced relation to a transversely disposed imaginary line that bisects spinal fusion implant 5.

This fifth embodiment also adds anti-retraction teeth 70 to upper and lower surfaces 25 and 30. Teeth 70 are swept back for insertion in a proximal-to-distal direction and such directional sweeping inhibits distal-to-proximal retraction.

Spinal fusion implant 5 is advanced horizontally, distal end first, into the gap between the upper and lower vertebral bodies so that main body 10 is disposed in disc space DS (FIG. 2), with upper surface 25 engaging the lower endplate of the upper vertebral body and lower surface 30 engaging the upper endplate of the lower vertebral body, and with the fixed vertical retention plate 140 on proximal end 20 engaging the upper and lower vertebral bodies. Retention plate 35 on distal end 15 is extended away from main body 10, to avoid binding from the upper and lower vertebral bodies, deployed so that it is misaligned to main body 10 and retracted using rod 55.

Thus it is understood that the spine is locked in sandwiched relation between vertical retention plate 140 on the proximal side and retention plate 35 on the distal side even though only one incision has been made, said incision being on said proximal side. Retention plate 35 on the distal side is deployed into position by rotation of rod 55 and no incision is made on said distal side, thereby distinguishing the invention from prior art implants that require two (2) incisions, i.e., incisions on both the proximal and the distal side of the spine. Rod 55 may be provided with a tool-engageable head to facilitate its rotation.

Spinal fusion implant 5 is sized so that the distance between upper surface 25 and lower surface 30 is substantially the same as the height of the disc that the spinal fusion implant replaces, so that the proper spacing of the vertebral bodies can be maintained.

Figure 6:
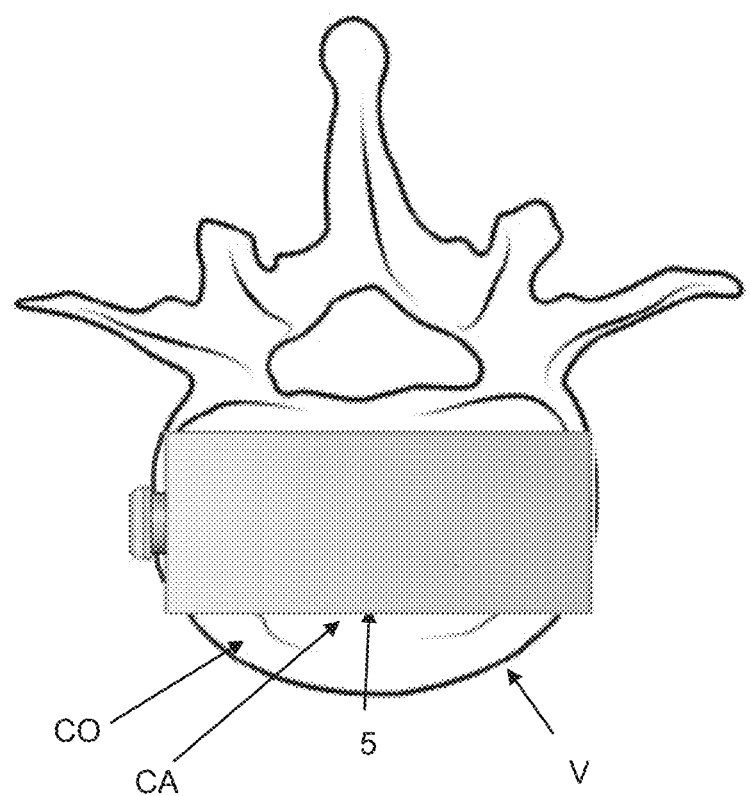
FIG. 6 is a schematic view illustrating the spinal fusion implant installed with the retention plate deployed outside of the vertebral body.

Spinal fusion implant 5 is also sized so that it can span cancellous portion CA of vertebral body V, with its proximal and distal ends resting on diametrically opposed portions CO of vertebral body V (FIG. 6). As a result, spinal fusion implant 5 supports the affected segment of the spine and immobilizes the affected segment of the spine, thereby facilitating fusion between the opposing vertebral bodies.

Apertures 50 permit the cancellous bone CA of the upper vertebral body and the cancellous bone CA of the lower vertebral body to grow into spinal fusion implant 5 to further facilitate bone fusion. Apertures 50 may be filled with a bone growth promoter.

Spinal fusion implant 5 is inserted into a disc space using a lateral approach. The lateral approach is preferred because it is familiar to spine surgeons, and also minimizes the possibility of damage to the spinal cord during insertion of the spinal fusion implant.

An instrument is first used to determine the disc plane VP of the disc space which is to receive spinal fusion implant 5. Properly identifying the disc plane of the disc space is important because disc plane VP may be used to identify the proper position for disc space DS to receive the spinal fusion implant.

At least one of the instruments preferably includes a directional feature which is used to maintain alignment of the instrumentation with the vertical plane of the intervertebral joint. By way of example but not limitation, a directional cannula may include a flat portion and the remaining instruments may include a flat portion on an opposite portion of the instrument, so that the instruments may be inserted through the cannula at zero degrees (0°) or one hundred eighty degrees (180°) only.

After disc space DS has been formed, spinal fusion implant 5 is inserted into disc space DS so that substantially main body 10 spans the gap between the opposing vertebral bodies, with lower surface 30 resting on the upper endplate of the lower vertebral body and upper surface 25 supporting the lower endplate of the upper vertebral body, with vertical retention plate 140 engaged with the upper and lower vertebral bodies. Retention plate 35 then is deployed to the misaligned position and retracted by rod 55 to engage the upper and lower vertebral bodies to lock the upper and lower vertebral bodies against lateral and torsional movement, etc. relative to spinal fusion implant 5 and relative to each other.

Preferably, spinal fusion implant 5 is slightly oversized relative to disc space OS so as to create a press fit. Spinal fusion implant 5 provides the stability and strength needed to immobilize the vertebral bodies while fusion occurs. Due to the non-circular cross-section of substantially parallelepiped body 10 and the disposition of the opposing vertebral bodies, spinal fusion implant 5 will hold the opposing vertebral bodies stable relative to one another.

If spinal fusion implant 5 is formed out of a sufficiently strong and rigid material, disc space DS may not need to be pre-formed from the disc and the opposing vertebral bodies. In this case, the spinal fusion implant may be simply tapped into place, in much the same manner that a punch is used.

Figure 14:
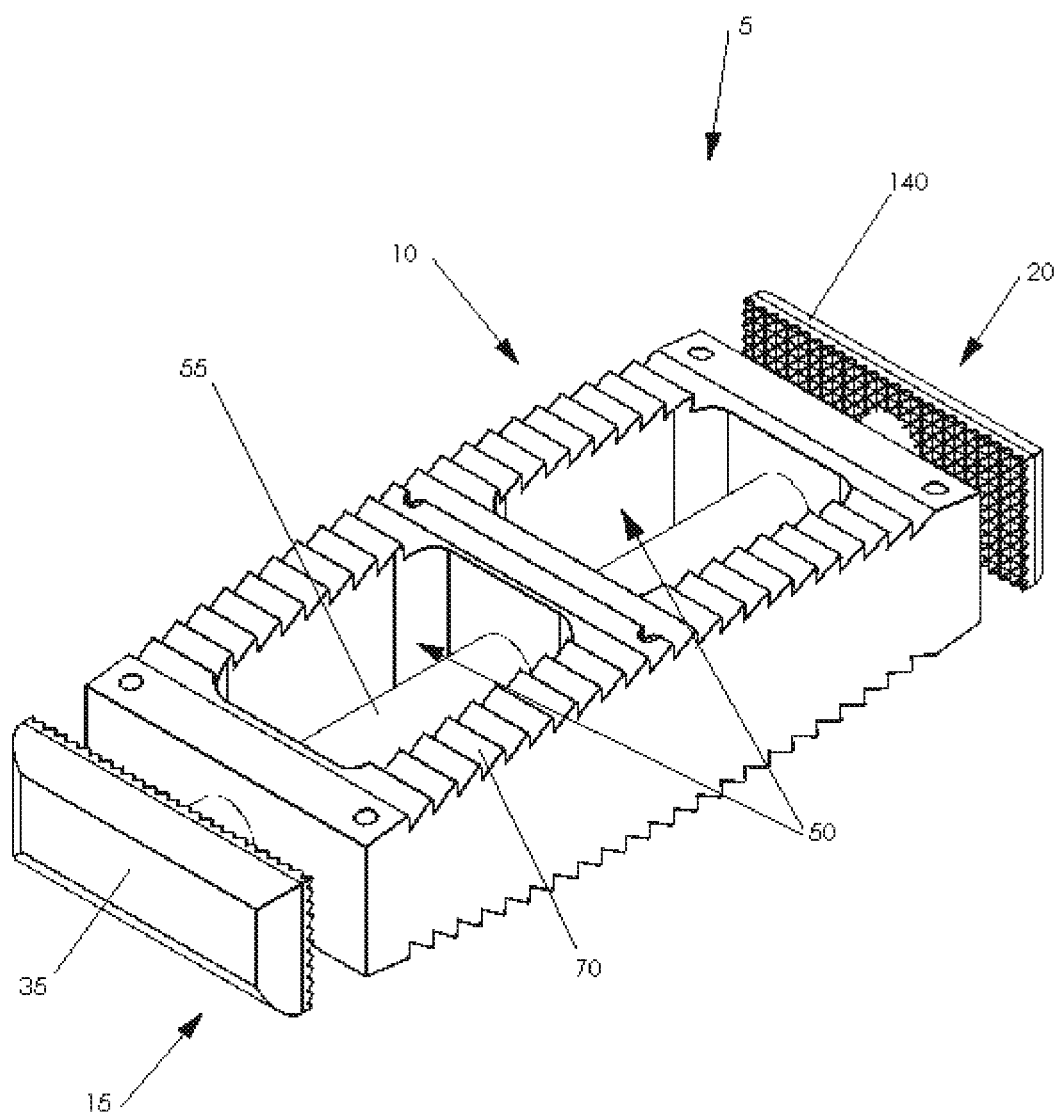
FIG. 14 is a perspective view of a sixth embodiment.
Figure 15:
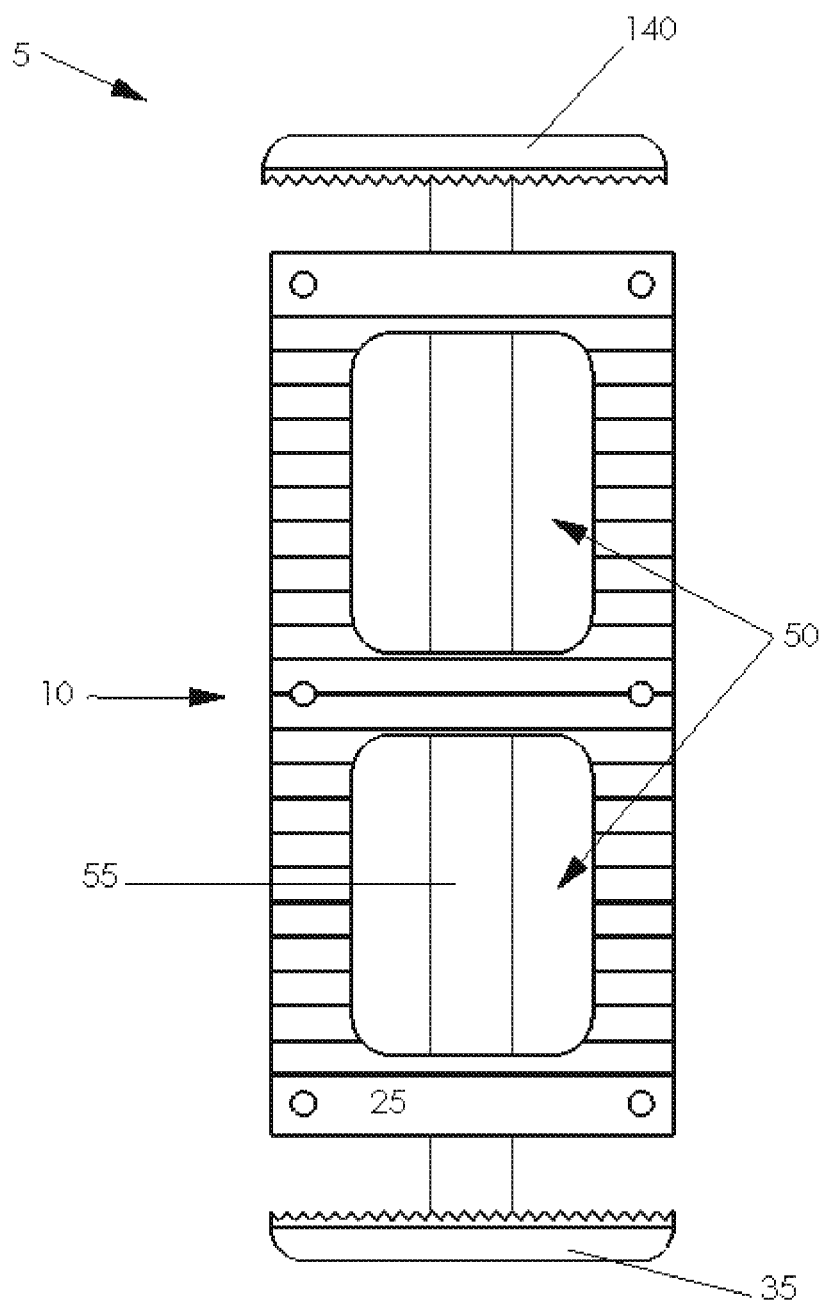
FIG. 15 is a top plan view of said sixth embodiment.

The sixth embodiment is depicted in FIGS. 14-15. It is similar to the fifth embodiment but it lacks spacer 60.

Figure 16:
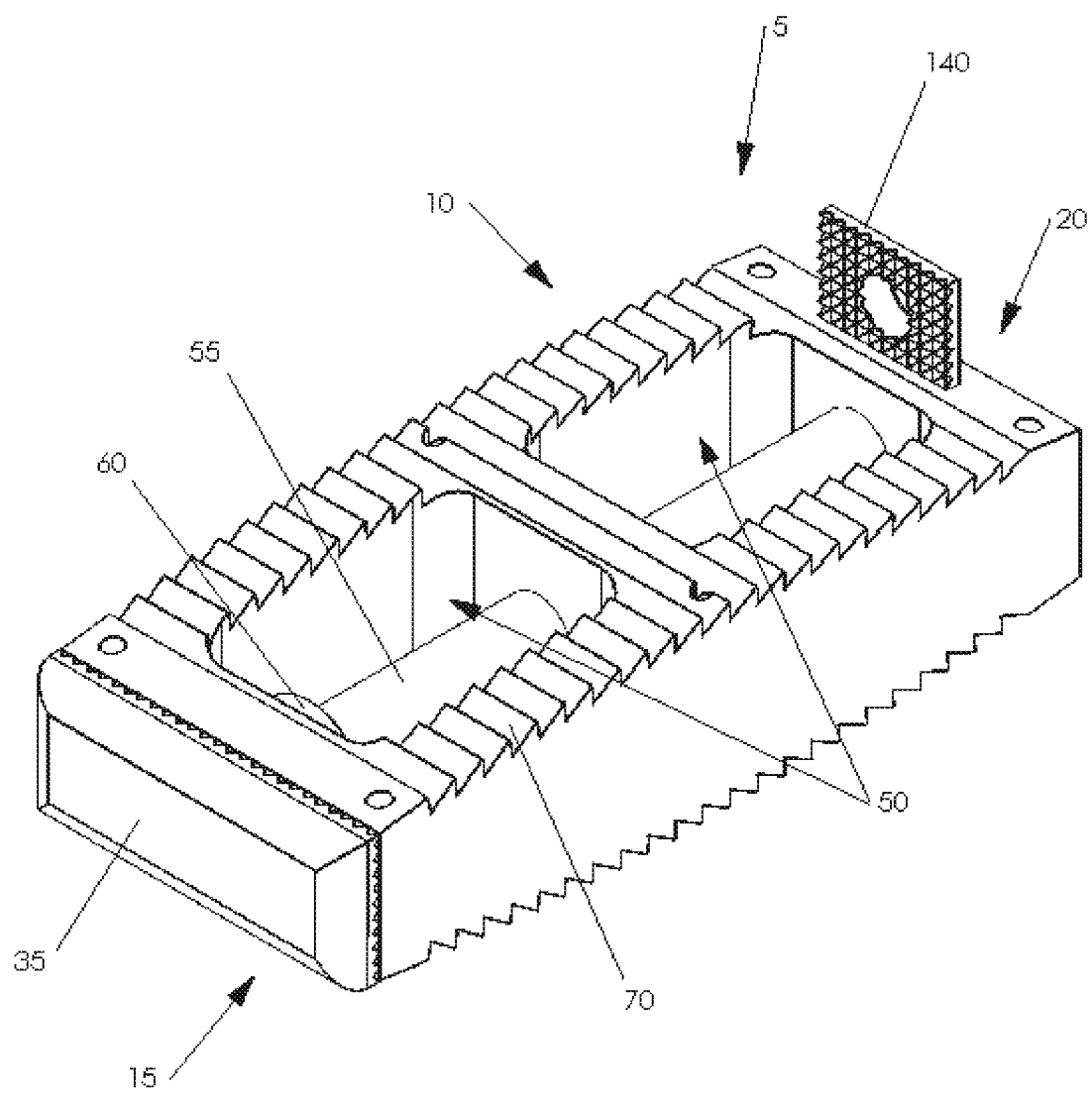
FIG. 16 is a perspective view of a seventh embodiment.
Figure 17:
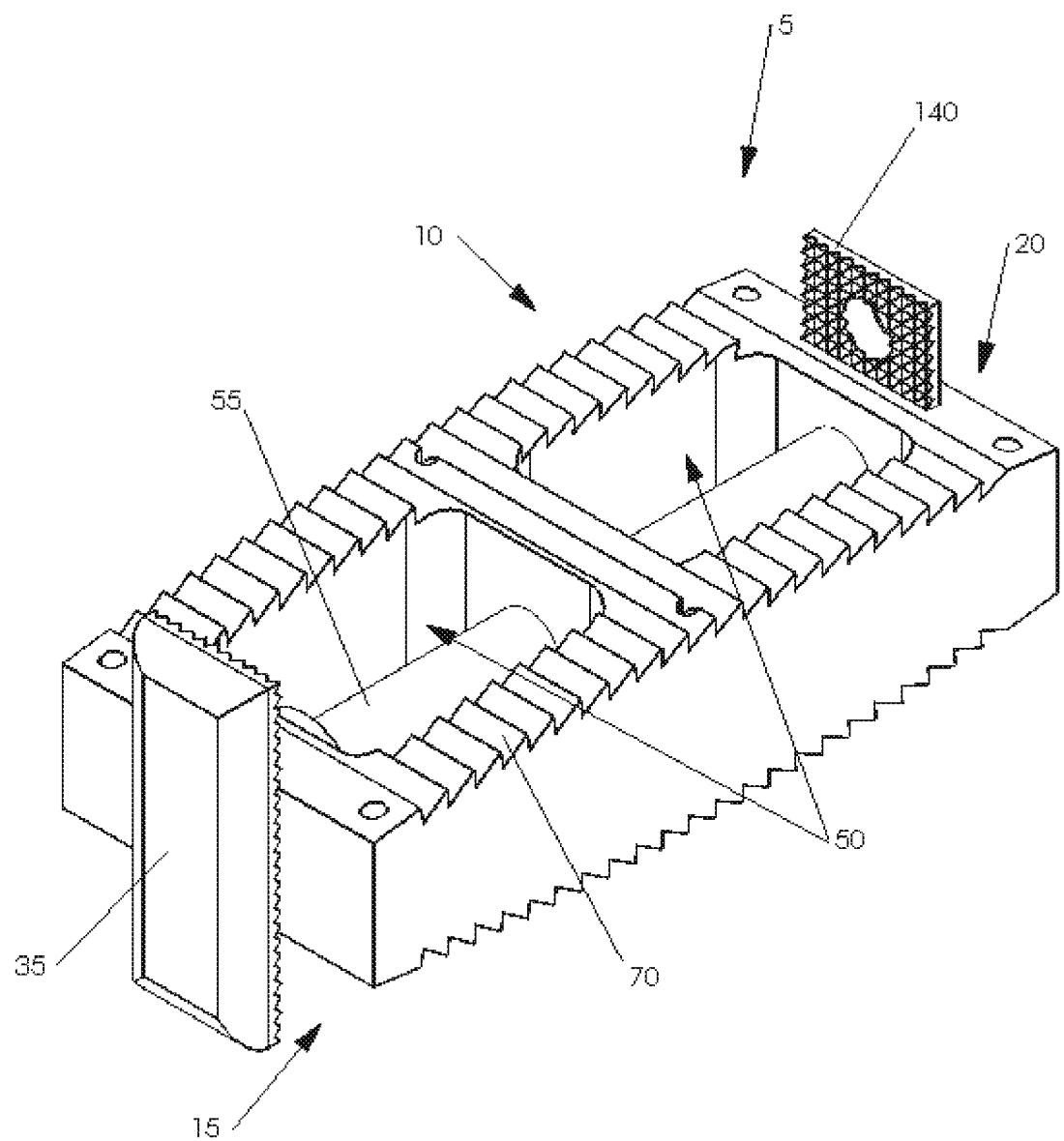
FIG. 17 is a perspective view similar to FIG. 16 but with the distal retention plate in its deployed configuration.
Figure 18:
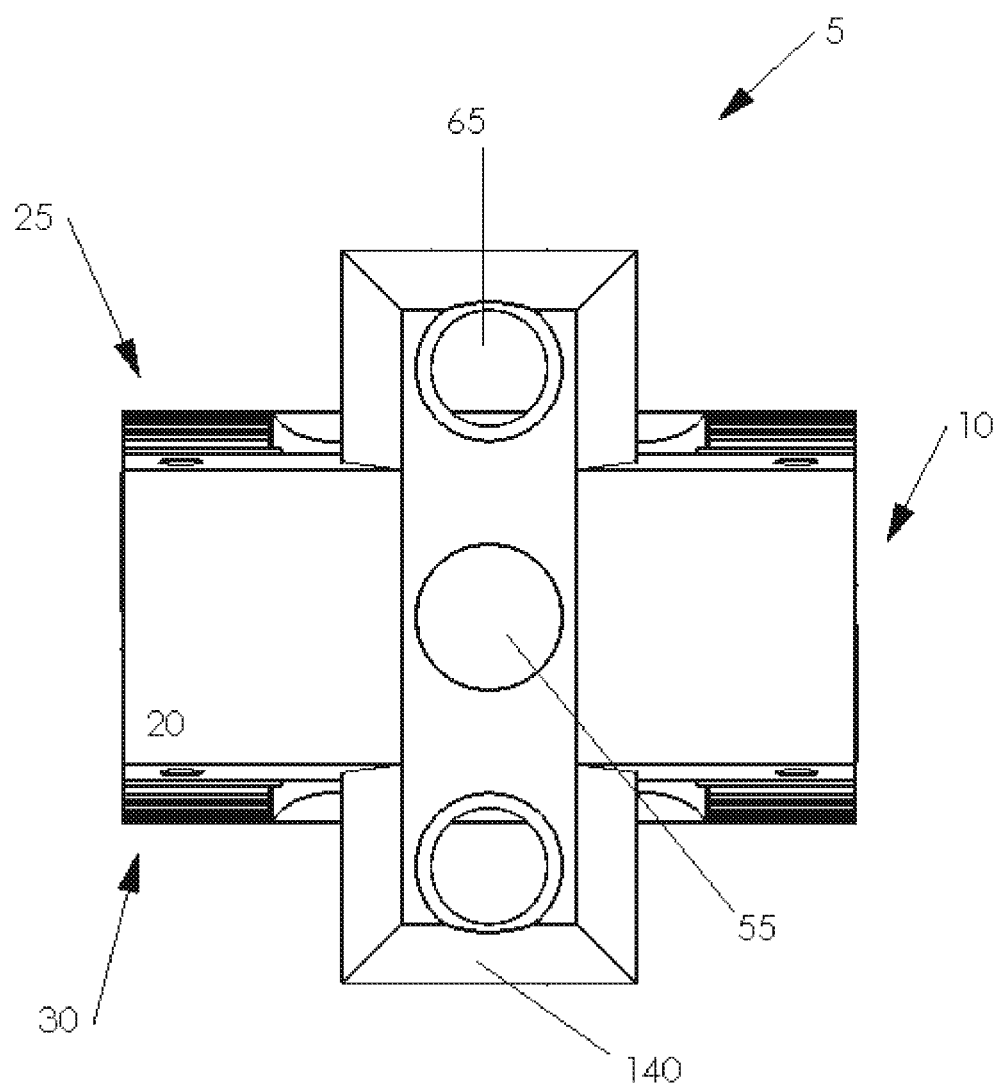
FIG. 18 is an end view of the seventh embodiment.

The seventh embodiment is depicted in FIGS. 16-18. In this embodiment, proximal retention plate 140 is permanently mounted in perpendicular relation to the plane of main body 10, i.e., said proximal retention plate is not rotatably mounted. Distal retention plate 35 is rotatably mounted on rod 55 because it must be undeployed when device 5 is inserted. Openings 65 are provided to receive screws or other suitable fastening means to enhance the connection between the device and the vertebrae.

Figure 19:
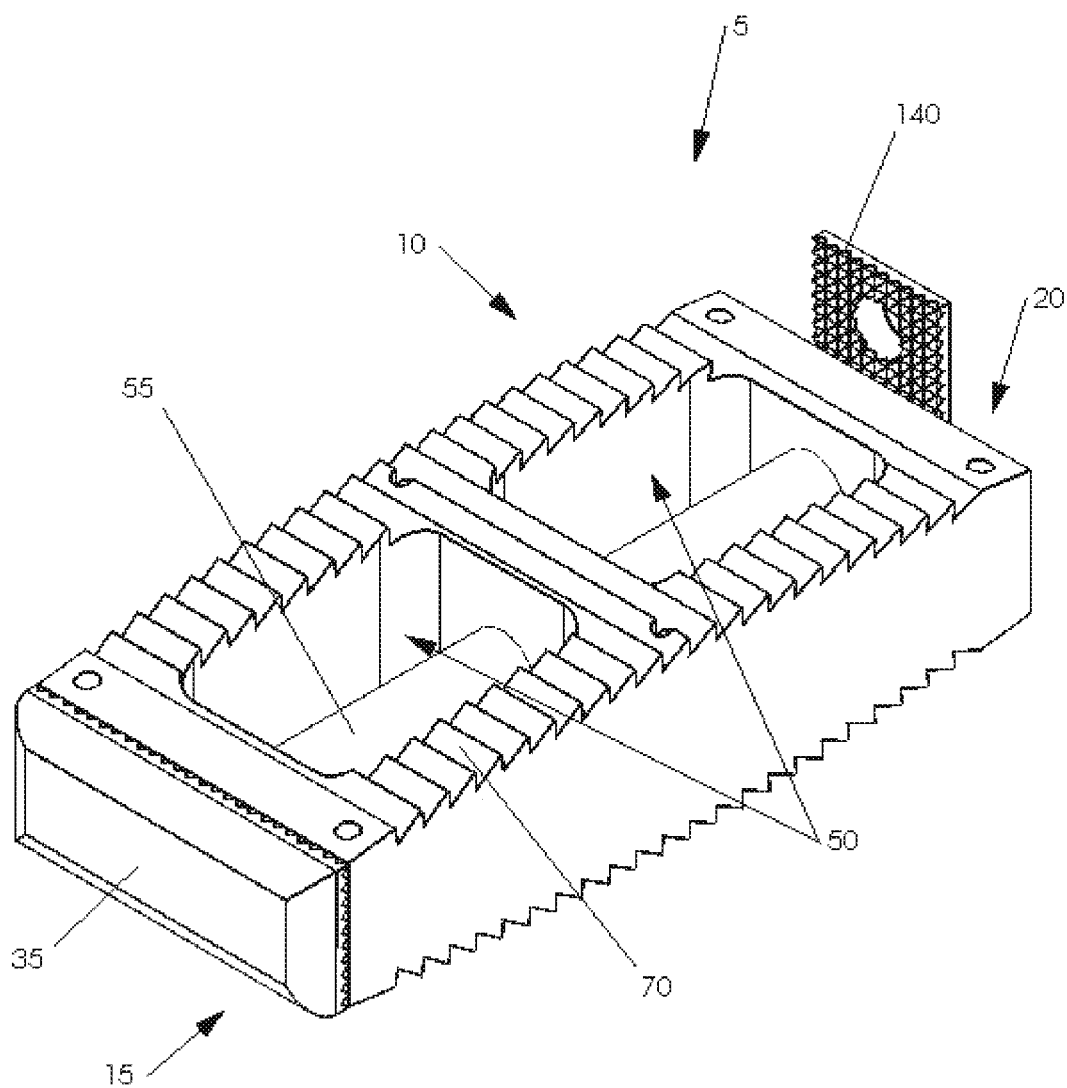
FIG. 19 is a perspective view of an eighth embodiment.
Figure 20:
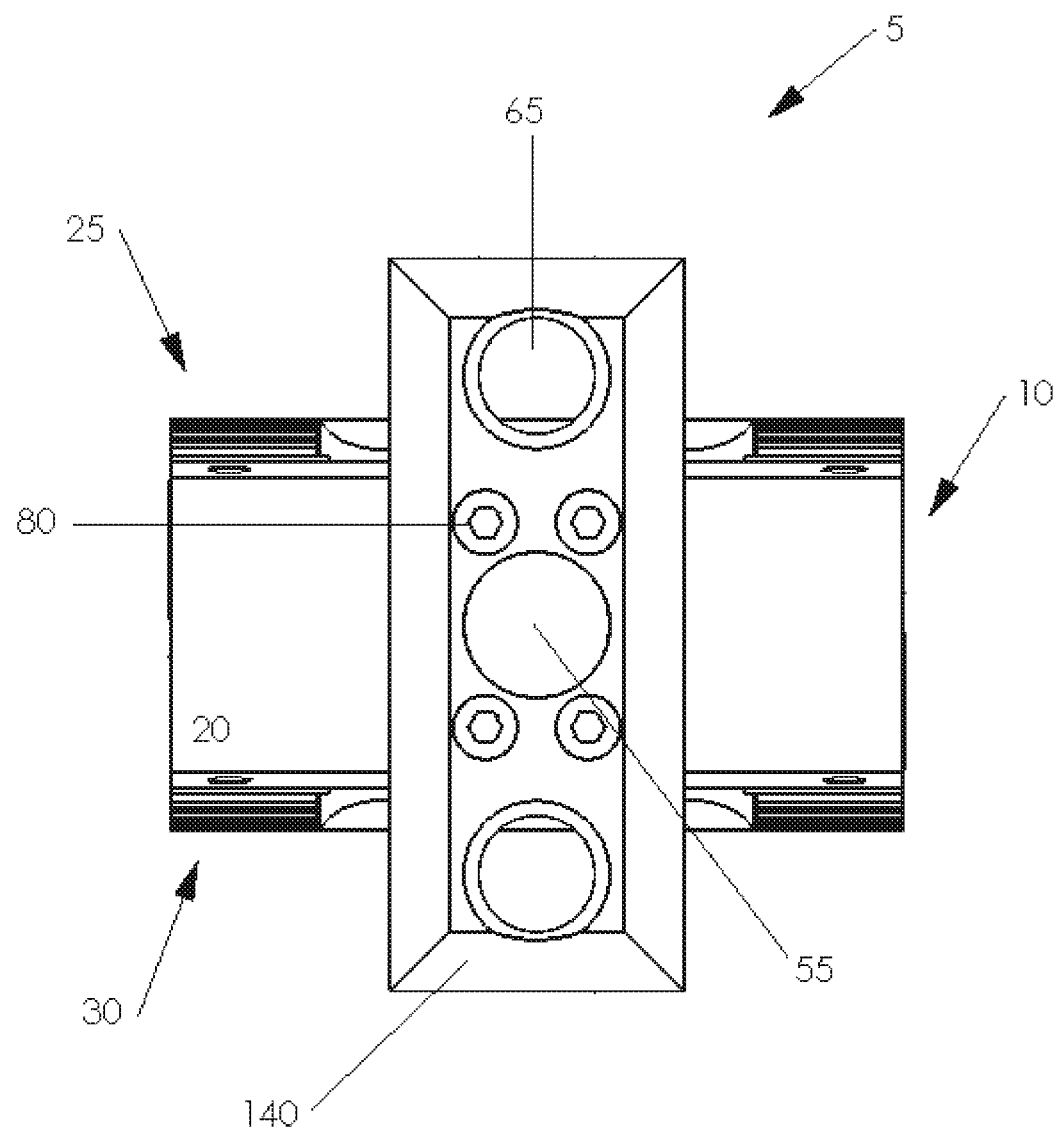
FIG. 20 is an end view of the eighth embodiment.

FIGS. 19 and 20 depict the eighth embodiment. Proximal retention plate 140 in this embodiment is not embedded within main body 10 as depicted in FIGS. 16-18 but is instead secured against rotation by tool-engageable bolts 80 or other suitable fastening means in overlying relation to the proximal end of main body 10. Distal retention plate 35 is attached to rod 55 and is free to deploy into locking position.

Figure 21:
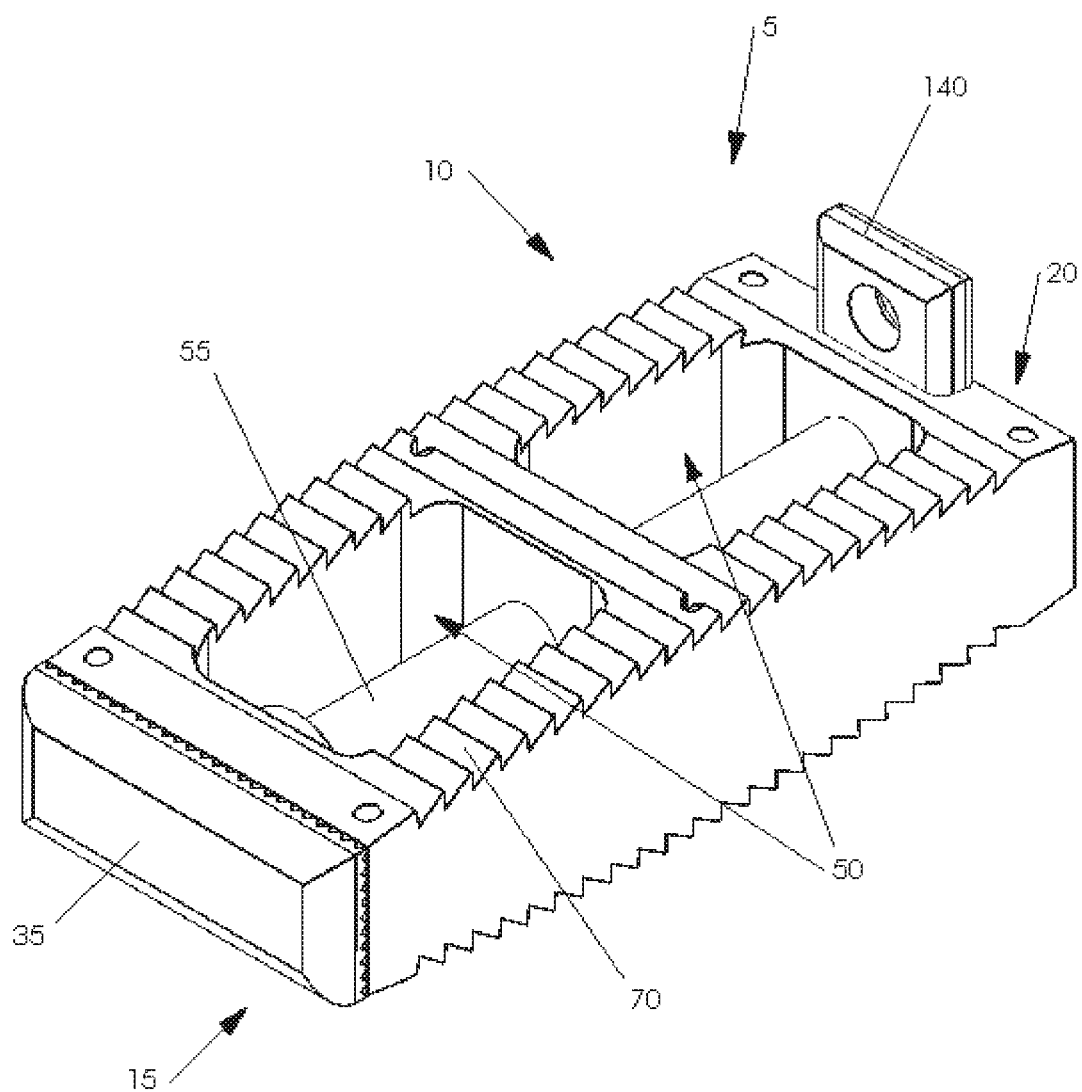
FIG. 21 is a perspective view of a ninth embodiment.
Figure 22:
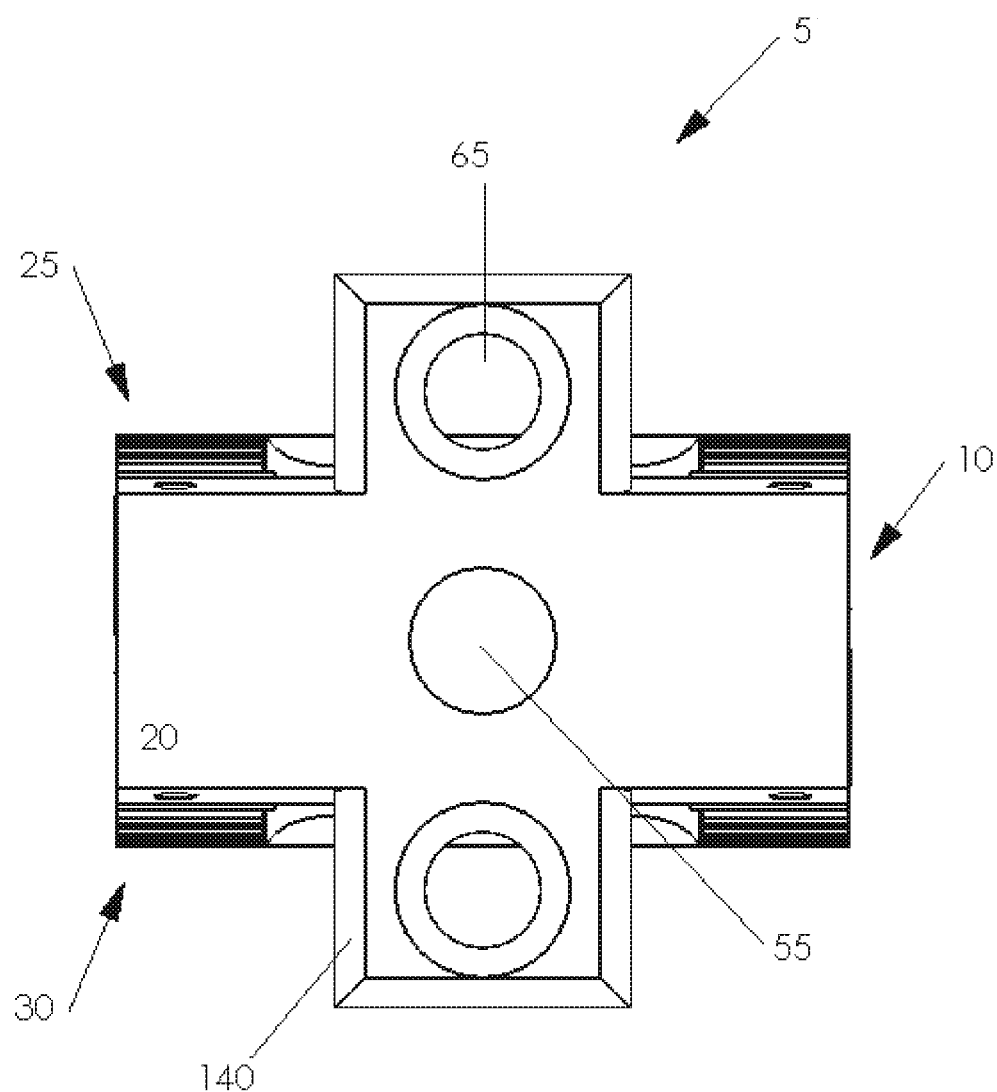
FIG. 22 is an end view of the ninth embodiment.

The ninth embodiment is depicted in FIGS. 21-22. As best depicted in FIG. 22, proximal retention plate 140 is integrally formed with the proximal end of main body 10 and thus has a fixed position. Said proximal retention plate has an upwardly protruding section that extends above upper surface 25 and a downwardly protruding section that extends below lower surface 30. Openings 65 are provided to receive screws or other suitable fastening means to enhance the connection between the device and the vertebrae.

Figure 23:
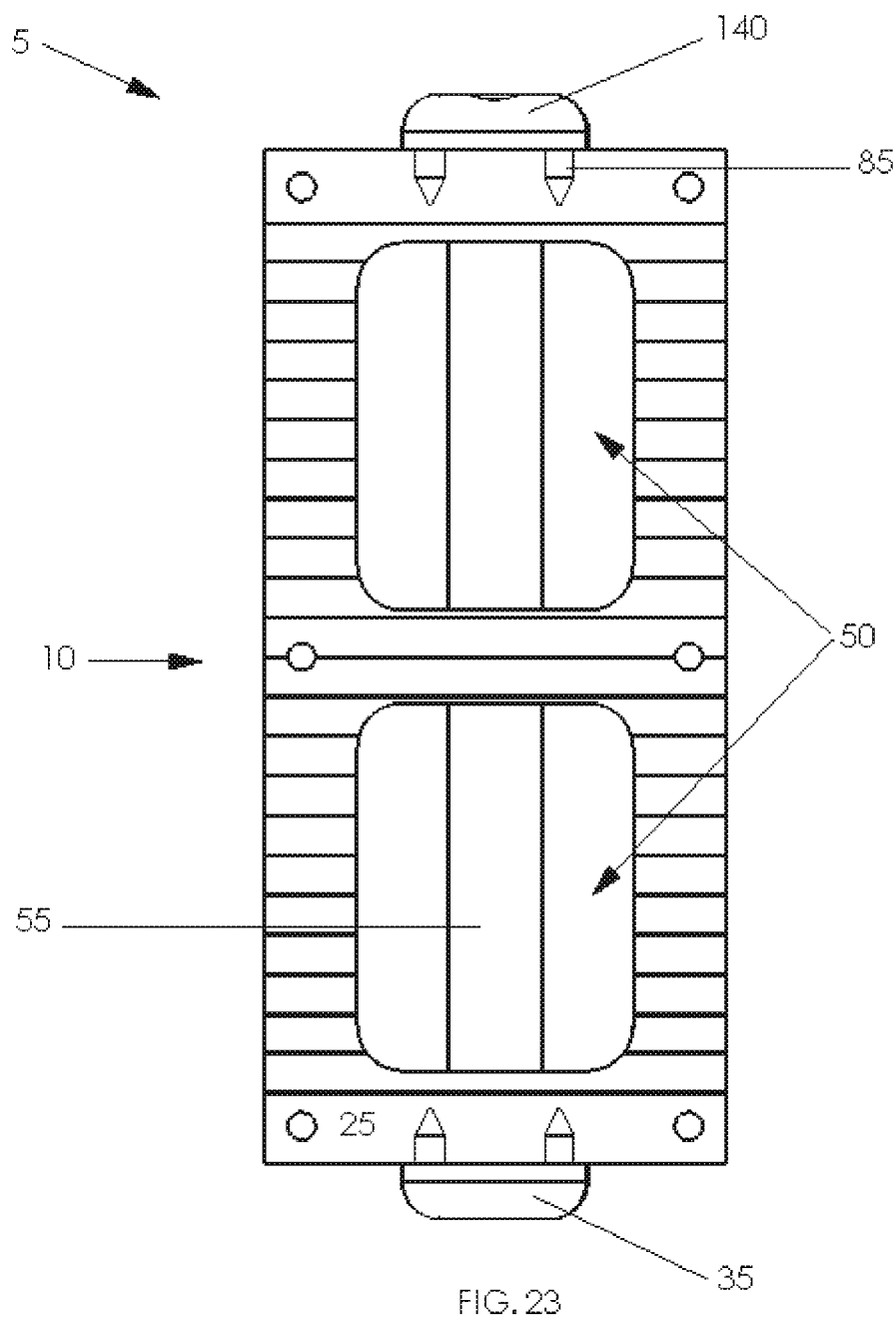
FIG. 23 is a top plan view of a tenth embodiment.
Figure 24:
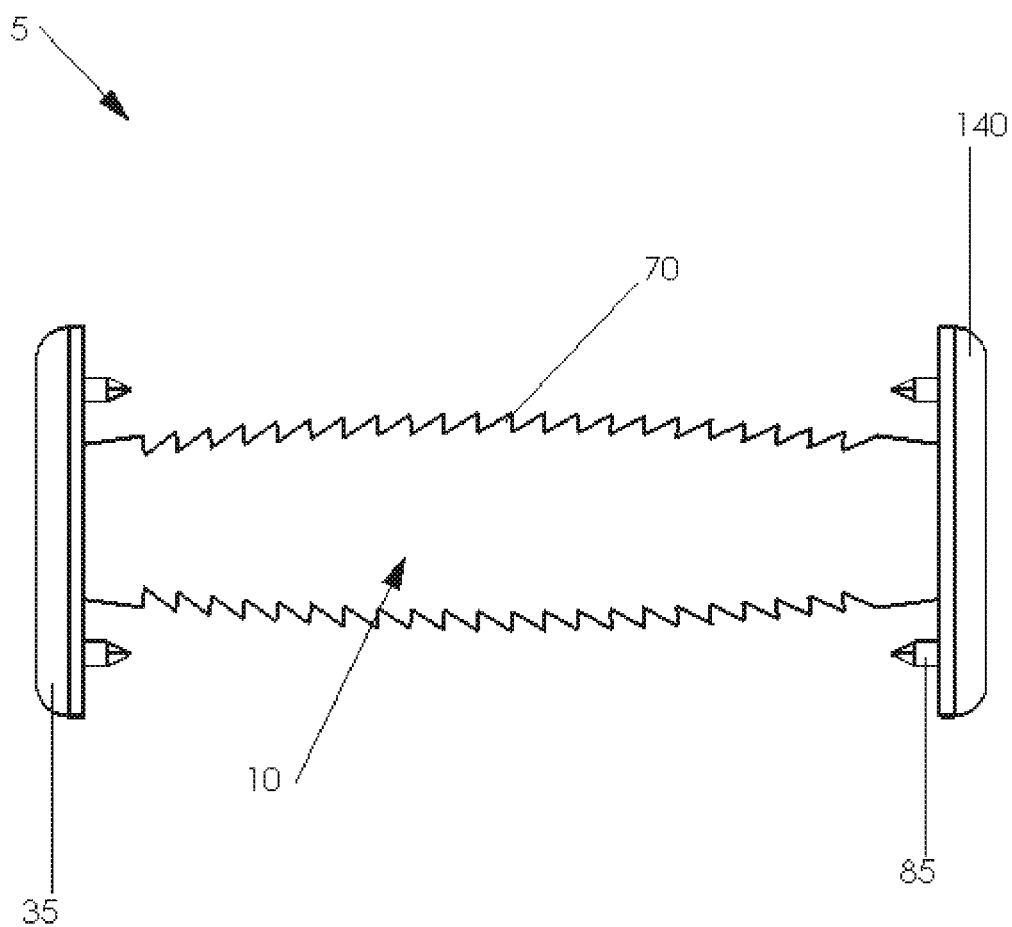
FIG. 24 is a side elevational view of the tenth embodiment.
Figure 25:
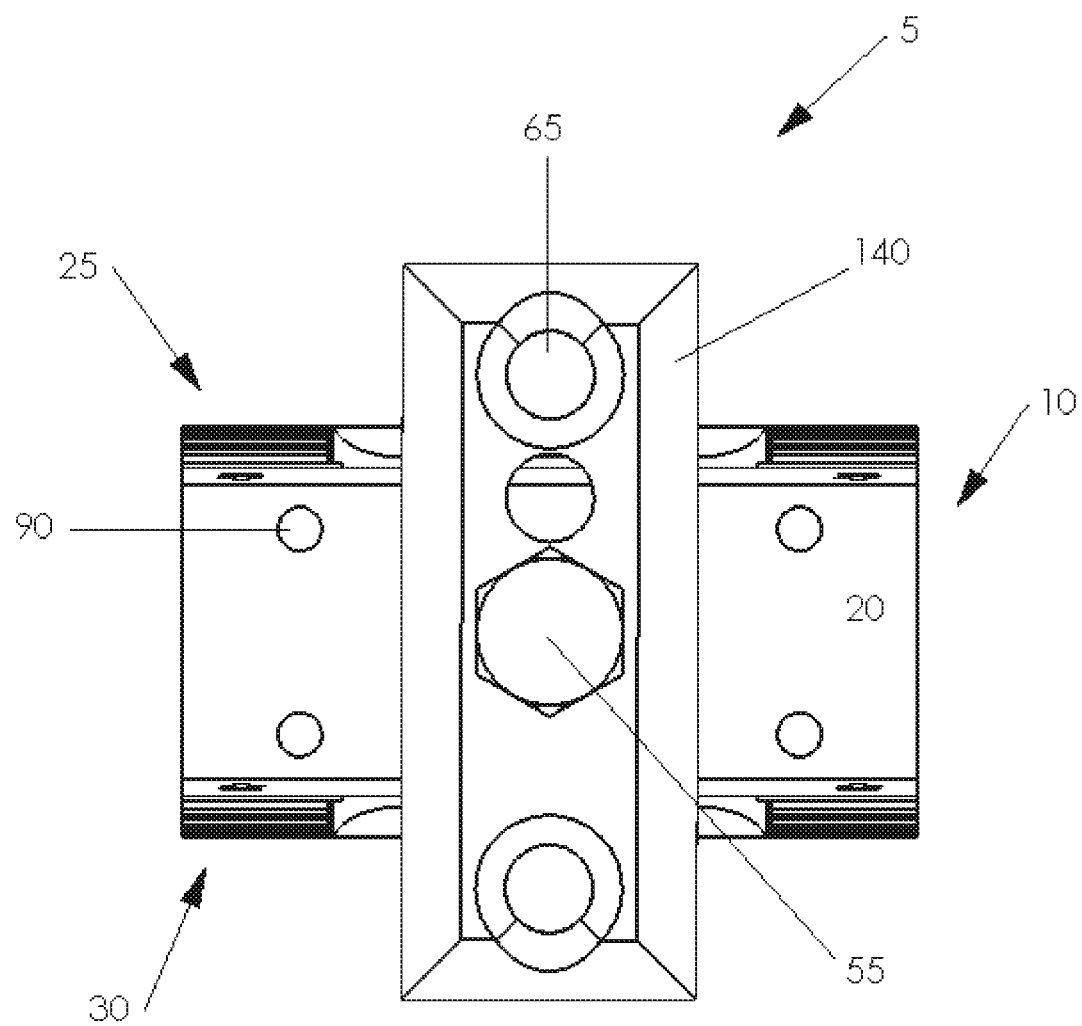
FIG. 25 is an end view of the tenth embodiment.

FIGS. 23-25 depict the tenth embodiment. Protuberances, collectively denoted 85, are formed in the respective inboard surfaces of distal and proximal retention plates 35 and 140, respectively. Protuberances 85 engage their adjacent vertebrae and thus further secure device 5 against movement. The protuberances are disposed within openings 90 (FIG. 25) when the retention plates are not rotated, i.e., coplanar with main body 10.

The protrusions collectively denoted 85 are preferably provided on retention plates 35 and 140 respectively to provide an additional means of affixing spinal fusion implant 5 to upper and lower vertebrae. However, only one (1) protrusion is within the scope of this invention.

Figure 26:
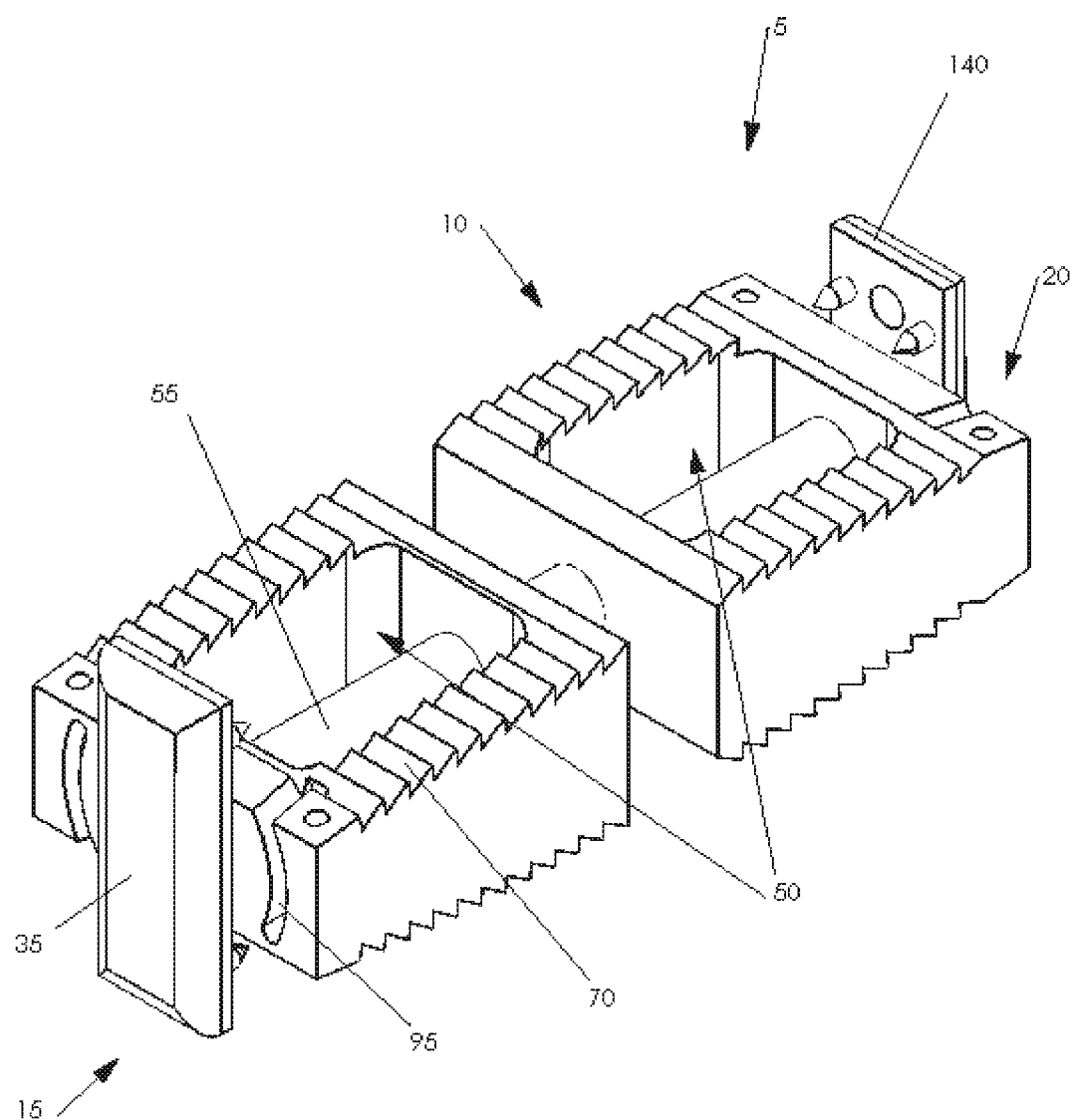
FIG. 26 is a perspective view of a eleventh embodiment.

Embodiment eleven is depicted in FIG. 26. This embodiment adds arcuate recesses 95 to accommodate protuberances 85. Distal retention plate 35 has been rotated from its coplanar position with main body 10 to its depicted position by a counterclockwise rotation and proximal retention plate 140 has been rotated from its coplanar position with main body 10 to its depicted position by a clockwise rotation.

This eleventh embodiment also discloses that the proximal and distal halves of main body 10 may be formed of two distinct pieces so that said proximal and distal ends may be spaced apart from one another as depicted when lengthening of device 5 is required. Main body 10 is divided into two parts along a parting line that is transverse to a longitudinal axis of symmetry of said main body so that its proximal and distal ends can be spaced apart from one another as depicted, maintained in cooperative alignment with one another by central rod 55. The central rod has a first length substantially equal to the predetermined length of the main body and an infinite plurality of second lengths greater than said predetermined length. More particularly, the central rod has two parts that are screwthreadedly secured to one another so that relative rotation between the two parts in a first direction lengthens the central rod and relative rotation between the two parts in a second direction shortens the central rod. The two independently formed sections of the main body are disposed in abutting relation to one another when the central rod is at its first length and the two independently formed sections of the main body are disposed in longitudinally spaced apart relation to one another when the central rod is lengthened.

Figure 27:
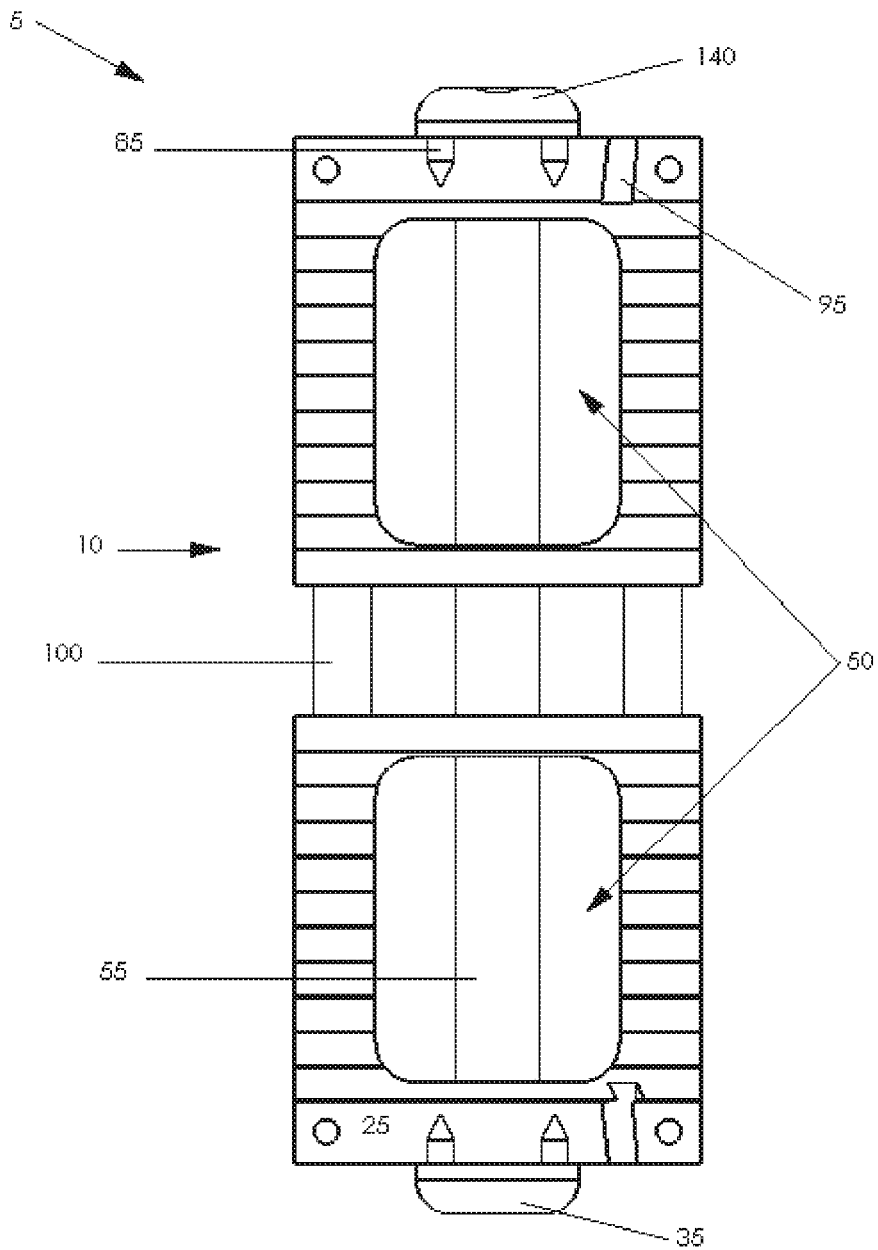
FIG. 27 is a top plan view of a twelfth embodiment.

Embodiment twelve is depicted in FIG. 27. This embodiment adds anti-rotation rods 100, parallel to rod 55 and disposed on opposite sides thereof, that interconnect the proximal and distal ends of main body 10 to one another and prevent relative rotation therebetween.

Figure 28:
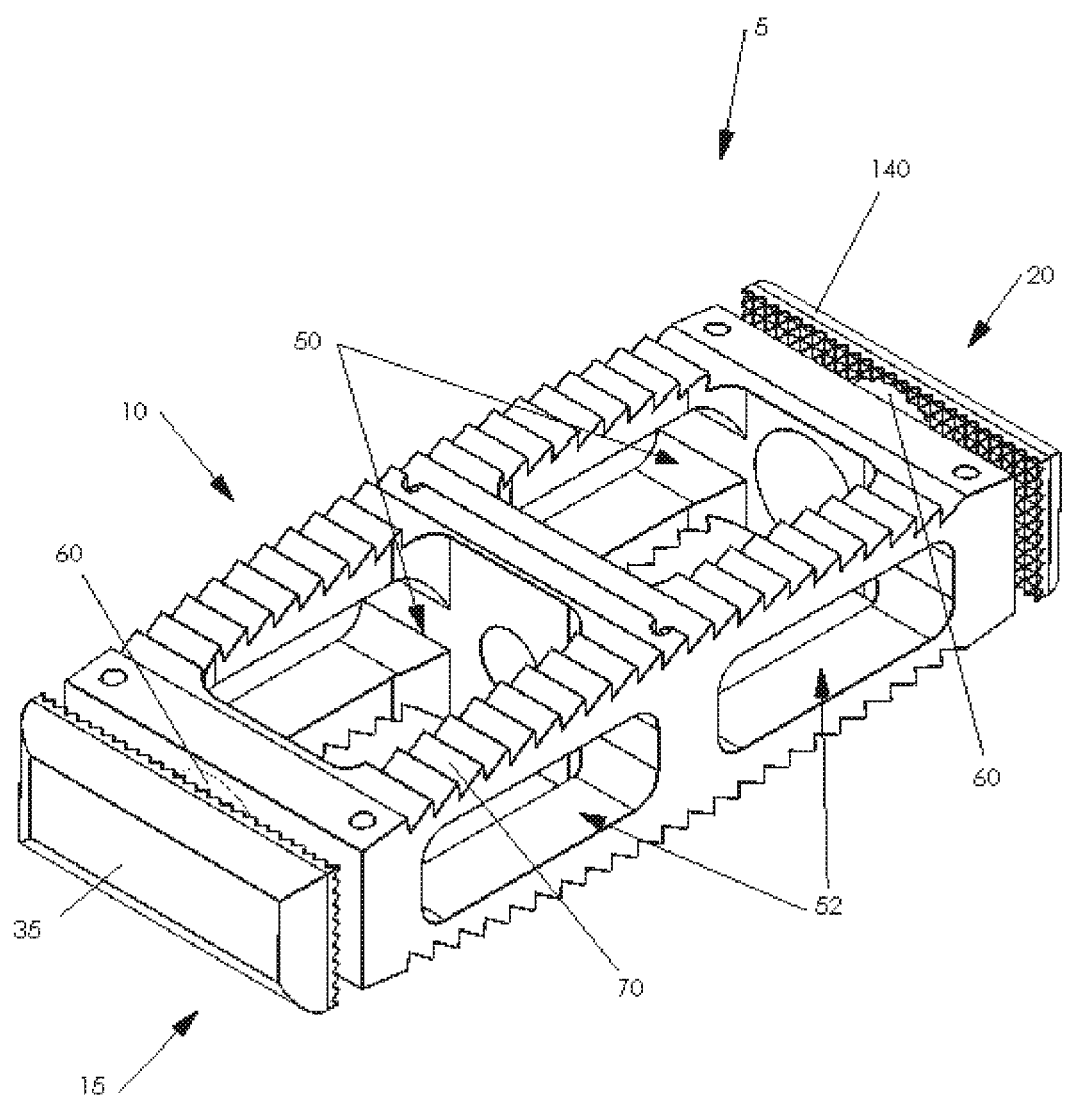
FIG. 28 is a perspective view of a thirteen embodiment

FIG. 28 depicts the thirteenth embodiment. This embodiment adds apertures 52 that extend horizontally through main body 10 and which are preferably in open communication with vertical apertures 50. Like vertical apertures 50, apertures 52 may be filled with bone growth promoting substance.

Figure 29:
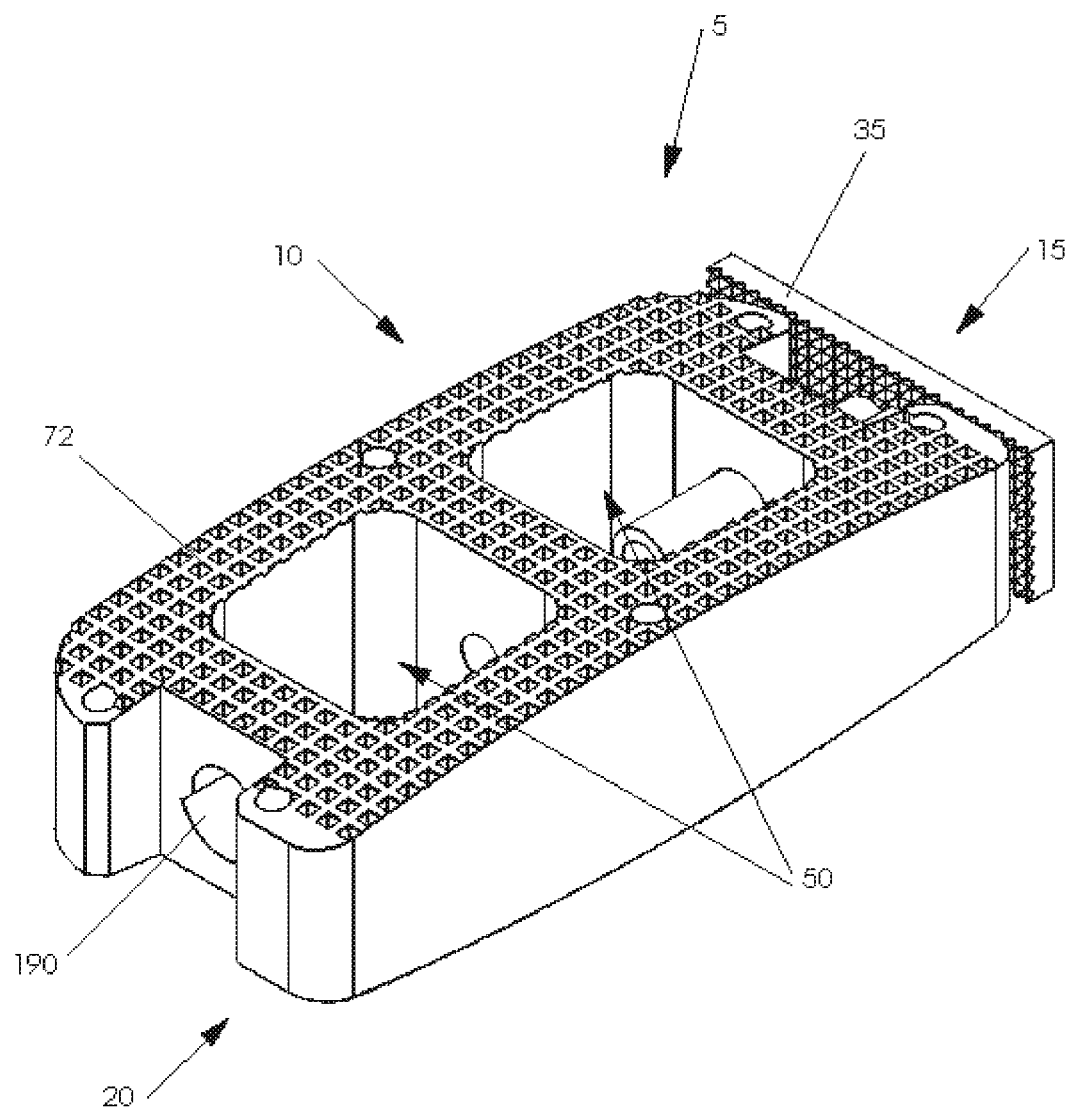
FIG. 29 is a perspective view of a fourteenth embodiment.

The fourteenth embodiment is depicted in FIGS. 29-30. Instead of anti-retraction teeth 70, the anti-retraction function is performed by protuberances or spikes, collectively denoted 72, formed in upper and lower surfaces 25 and 30. This embodiment also includes rotatably mounted distal retention plate 140 but no proximal retention plate is provided. The proximal end 20 of main body 10 is extended as depicted on opposite sides thereof and said extensions are covered with said protuberances 72 to provide traction. Such extensions are also provided at distal end 15.

This fourteenth embodiment also includes short adjustment shaft 195 with key 200 used to restrict deployment motion. Key 200 is received within non-circular port 190. The key way is the larger diameter portion of non-circular port 190 that allows the key to rotate over a fixed angle.

This embodiment further includes key way port 190 (FIG. 29) on proximal end 20 which enables insertion of an adjustment device, not depicted, for distal retention plate 35. Key way port 190 could also be used to hold a proximal retention plate. A proximal retention plate can be attached to the device after the distal retention plate is deployed. In all embodiments that depict distal retention plate only (FIGS. 3, 8, 29 and 34), a proximal retention plate may be attached to the device after the distal retention plate is deployed to enhance stability.

Figure 31:
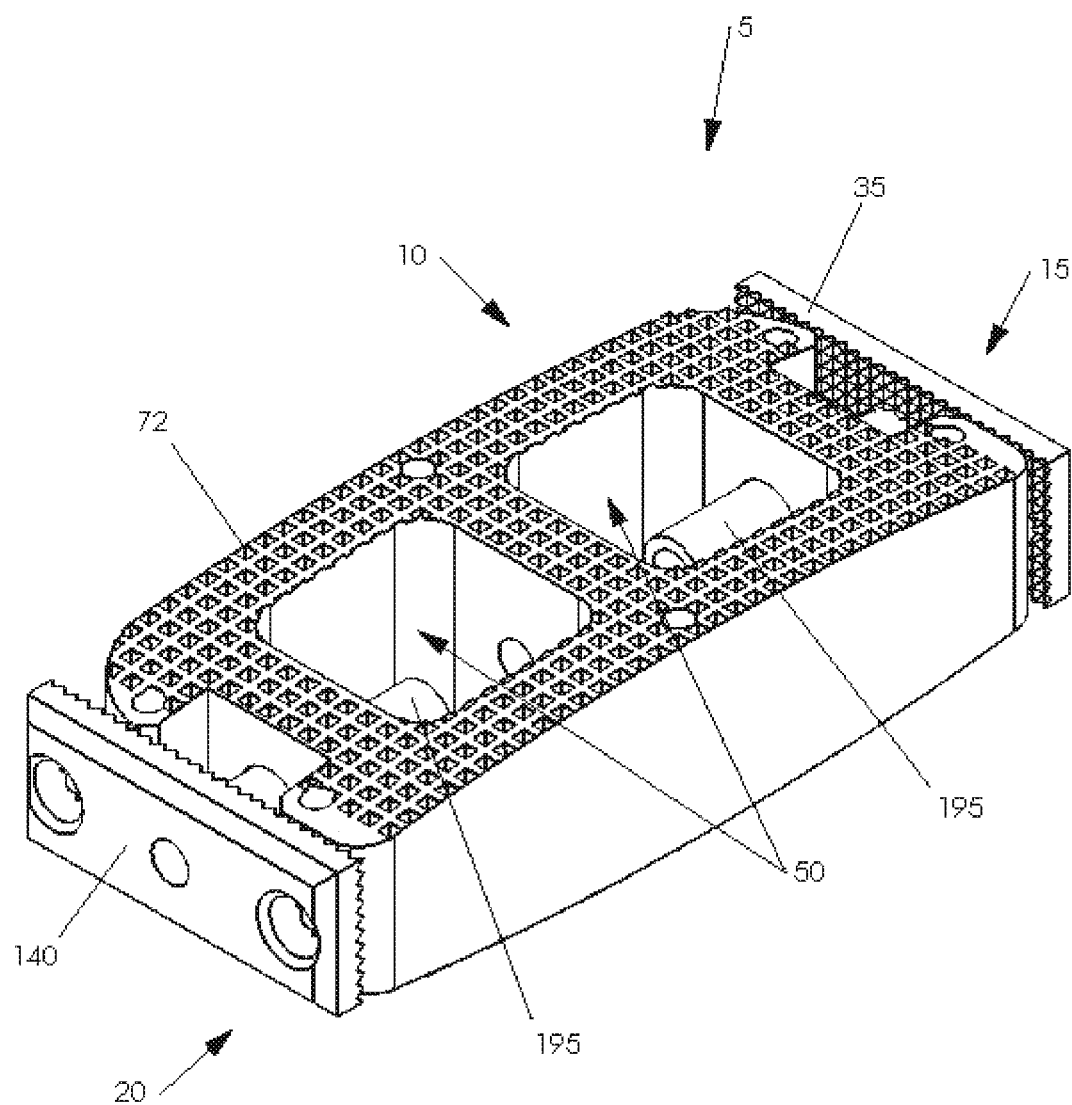
FIG. 31 is a perspective view of a fifteenth embodiment.

The fifteenth embodiment is depicted in FIG. 31. This embodiment is similar to embodiment number fourteen but this embodiment includes distal and proximal retention plates 35 and 140, respectively. The retention plates are mounted to cylindrical shafts 195. No anti-rotation key is provided on these shafts but such keys and associated keyways formed in main body 10 are within the scope of this invention.

Figure 32:
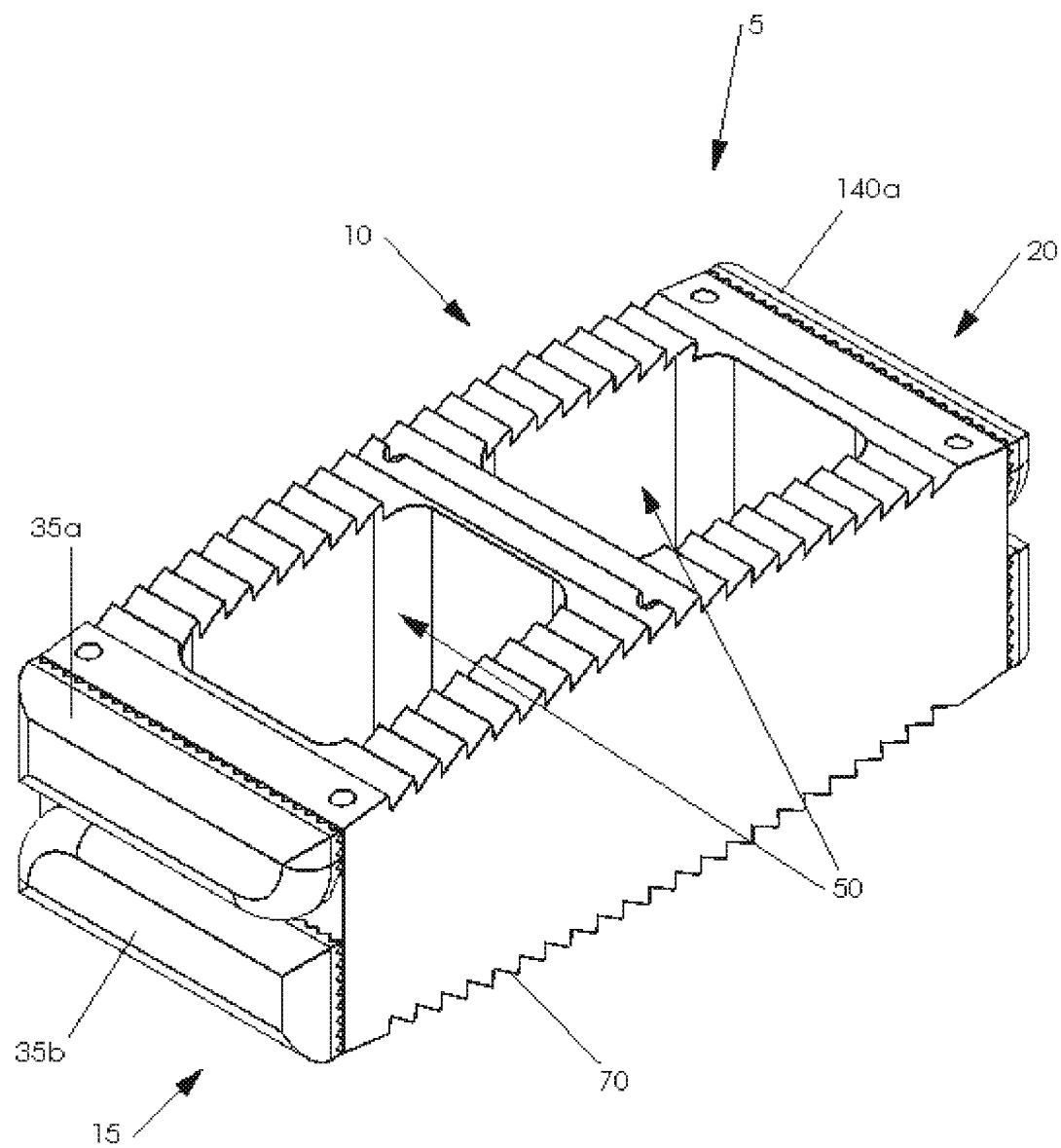
FIG. 32 is a perspective view of a sixteenth embodiment.
Figure 33:
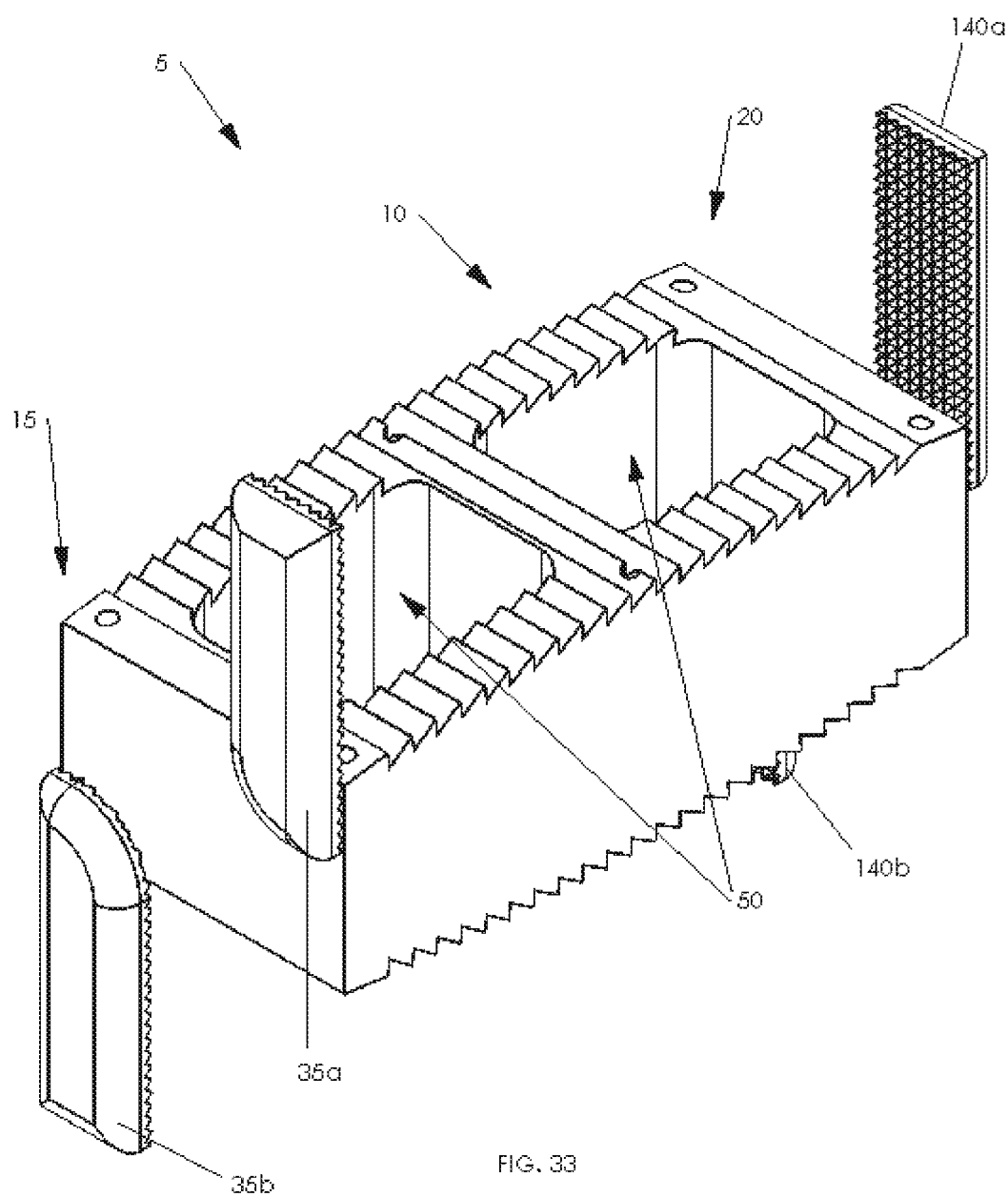
FIG. 33 is a perspective view of the sixteenth embodiment with its retention plates deployed.

The sixteenth embodiment is disclosed in FIGS. 32 and 33. Each distal and proximal retention plate is provided in two (2) separate parts 35a, 35b, and 140a, 140b, respectively. Each separate part is pivotally mounted for rotation from the undeployed positions of FIG. 32 to the deployed position of FIG. 33. The retention plates that are deployed above top surface 25 of main body 10 engage the superior vertebral body and the retention plates that are deployed below bottom surface 30 of main body 10 engage the inferior vertebral body.

As in all embodiments that include rotatable retention plates, said retention plates are initially in an undeployed, co-planar position with main body 10 when said main body 10 is inserted between adjacent vertebral bodies. The retention plates and subsequently rotated after main body 10 is inserted between adjacent vertebral bodies.

Figure 34:
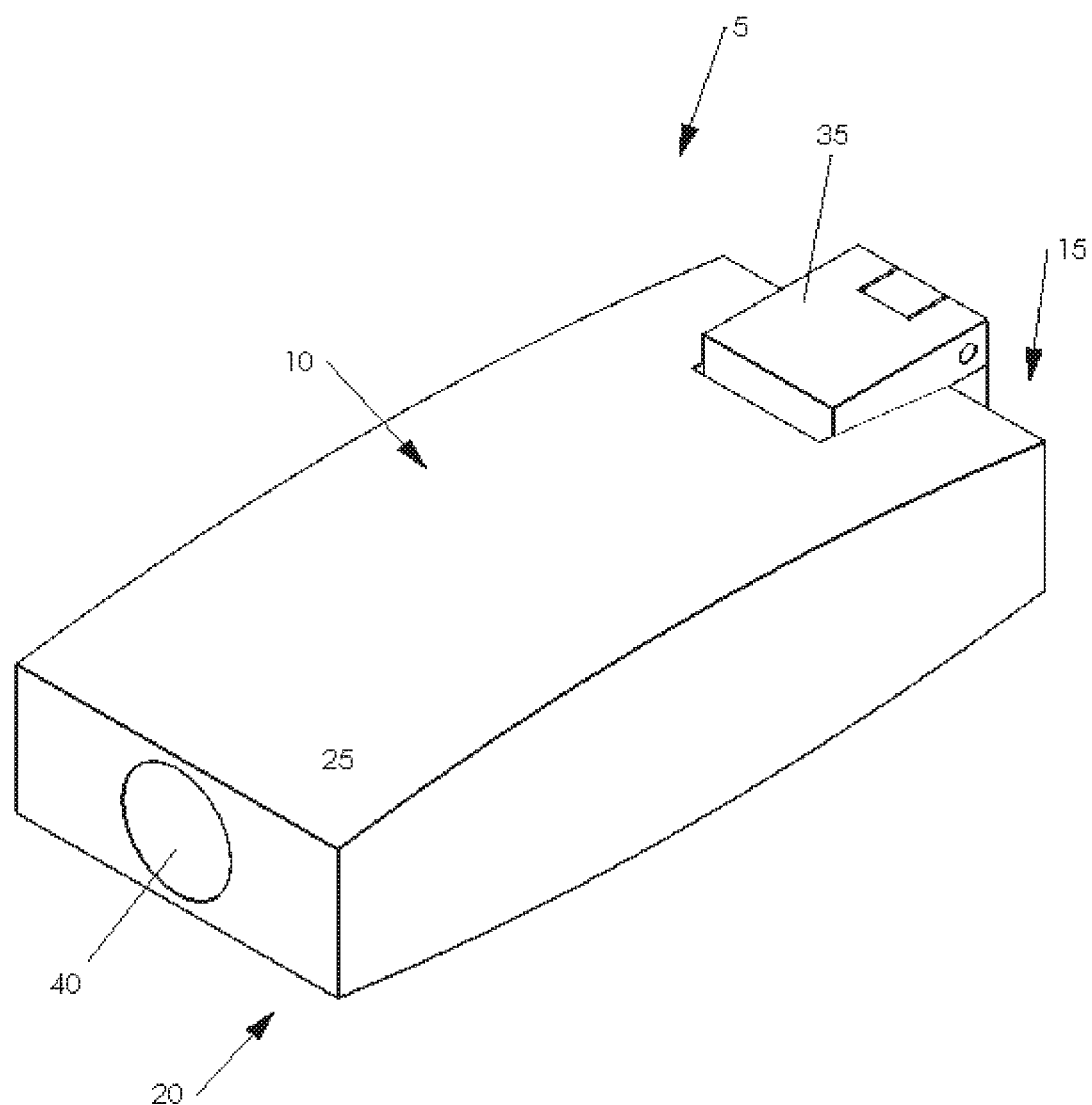
FIG. 34 is a perspective view of a seventeenth embodiment.
Figure 35:
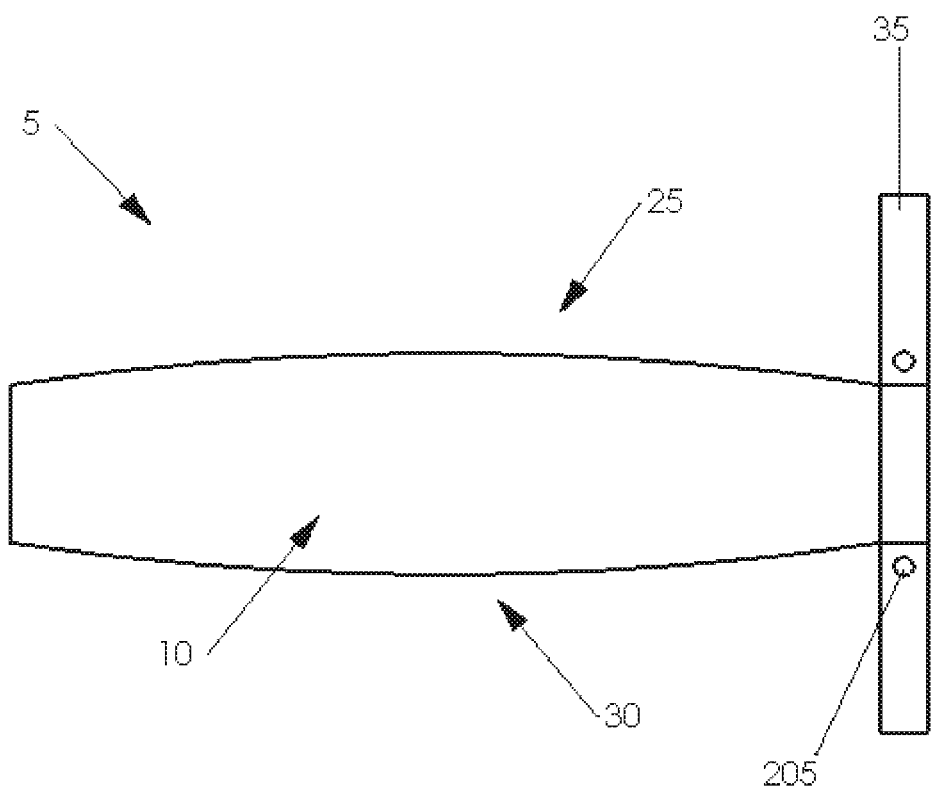
FIG. 35 is a side elevational view of the seventeenth embodiment but with the distal end retention plate in its deployed configuration.

FIGS. 34 and 35 depict the seventeenth embodiment. This embodiment includes hinged retention plate 35 on distal end 15 of main body 10.

FIG. 35 is a side view depicting retention plate 35 in a deployed position, flush against main body 10. Retention plate may be attached to main body 10 by rod 55, short shaft 195, or by spacers 60. The hinges are denoted 205.

The present invention provides a new and improved spinal fusion implant for facilitating vertebral body fusion. This innovative spinal fusion implant is able to withstand greater forces, prohibit motion in all directions and drastically reduce the risk of implant failure. The novel spinal fusion implant also eliminates the possibility of slippage during spinal motion, greatly improves vertebral body stability and promotes better inter-vertebral body fusion.

Numerous advantages are achieved by the present invention. Among other things, the present invention provides a fast, simple and easily reproduced approach for effecting spinal fusion. It also provides sufficient stabilization, where posterior plate or pedicle screws are not needed. Moreover, the present invention may be practiced using a minimally-invasive procedure or open surgical procedure.

While spinal fusion implant 5 has been disclosed in the context of fusing an intervertebral joint, it may also be used to stabilize and fuse any joint having anatomy similar to the intervertebral joint, i.e., a pair of opposing bony surfaces defining a gap therebetween, with the stabilizer of the fusion implant being sized to be positioned within the gap. By way of example but not limitation, the fusion implant may be used in small joints such as in the finger, toe, etc.

It will thus be seen that the objects set forth above, and those made apparent from the foregoing disclosure, are efficiently attained and since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A spinal fusion implant for insertion into an intervertebral disc space between adjacent, spaced apart vertebral bodies in a spinal joint, the spinal fusion implant comprising:

a generally parallelepiped main body having a predetermined length, width, and thickness, said main body having a proximal end and a distal end;

a rectangular distal retention plate having a distal end and a proximal end, the distal retention plate disposed at said distal end of said main body, said distal retention plate having (i) a first, non-rotated position that is co-planar with said main body, and (ii) a second, rotated position that is not co-planar with said main body, with a first portion of said distal retention plate extending above said main body such that said distal retention plate contacts a first vertebral body disposed above said main body, and a second portion of said distal retention plate extending below said main body such that said distal retention plate contacts a second vertebral body disposed below said main body;

a central rod having a distal end and a proximal end, said central rod being rotatably and slidably mounted to said main body, with said distal end of said central rod protruding from said distal end of said main body and said distal retention plate being fixedly mounted to said distal end of said central rod such that said distal retention plate rotates when said central rod is rotated, and with said proximal end of said central rod terminating distal to said proximal end of said main body; and a port formed in said proximal end of said main body, said port being aligned with said central rod such that said proximal end of said central rod is accessible from said proximal end of said main body to rotate and slide said central rod from said proximal end of said main body;

wherein said central rod is configured to (i) slide distally relative to said main body so as to displace said distal retention plate distally away from said distal end of said main body so as to adjust a distance between the distal end of the main body and the proximal end of said distal retention plate, (ii) rotate said distal retention plate from its first, non-rotated position to its second, rotated position, and (iii) displace said distal retention plate proximally toward said distal end of said main body so as to adjust a distance between said distal end of said main body and said proximal end of said distal retention plate, whereby to bring said first portion of said distal retention plate into contact with the first vertebral body disposed above said main body, and bring said second portion of said distal retention plate into contact with the second vertebral body disposed below said main body.

2. The spinal fusion implant according to claim 1, further comprising:

said main body being of substantially solid construction.

3. The spinal fusion implant according to claim 1 wherein the length of the main body is sufficient to span a distance between opposing cortical portions of one of the adjacent vertebral bodies without extending substantially beyond the vertebral body when the main body is inserted into the intervertebral disc space between the adjacent vertebral bodies.

4. The spinal fusion implant according to claim 1 wherein said distal retention plate is in said first, non-rotated position when said spinal fusion implant is inserted into the intervertebral disc space between the adjacent vertebral bodies.

5. The spinal fusion implant according to claim 1 wherein when said spinal fusion implant is inserted into the intervertebral disc space between the adjacent vertebral bodies and said distal retention plate is rotated to said second, rotated position, the first portion of the distal retention plate extends alongside the first vertebral body and the second portion of the distal retention plate extends alongside the second vertebral body, thereby preventing retraction of said main body from the intervertebral disc space in a distal-to-proximal direction, and thereby holding said spinal fusion implant and the adjacent vertebral bodies in a stable relationship to one another.

\* \* \* \* \*